United States Patent
Kenny et al.

(10) Patent No.: US 9,262,582 B2
(45) Date of Patent: Feb. 16, 2016

(54) DETECTION OF RISK OF PRE-ECLAMPSIA

(75) Inventors: Louise Kenny, Cork (IE); Philip Newton Baker, Edmonton (CA); David Broadhurst, Cork (IE)

(73) Assignee: University College Cork, National University of Ireland, Cork, Cork (IE)

( * ) Notice: Subject to any disclaimer, the term of this patent is extended or adjusted under 35 U.S.C. 154(b) by 510 days.

(21) Appl. No.: 13/515,323

(22) PCT Filed: Dec. 21, 2010

(86) PCT No.: PCT/EP2010/070446
§ 371 (c)(1),
(2), (4) Date: Sep. 14, 2012

(87) PCT Pub. No.: WO2011/080170
PCT Pub. Date: Jul. 7, 2011

(65) Prior Publication Data
US 2013/0073212 A1    Mar. 21, 2013

Related U.S. Application Data

(60) Provisional application No. 61/288,465, filed on Dec. 21, 2009.

(51) Int. Cl.
*G06F 19/24* (2011.01)
*G06F 19/10* (2011.01)
*G01N 33/68* (2006.01)

(52) U.S. Cl.
CPC .............. *G06F 19/24* (2013.01); *G01N 33/689* (2013.01); *G06F 19/10* (2013.01); *G01N 2800/368* (2013.01)

(58) Field of Classification Search
None
See application file for complete search history.

(56) References Cited

FOREIGN PATENT DOCUMENTS

WO    2006/867321 A2    8/2006

OTHER PUBLICATIONS

Kenny et al., "Novel biomarkers for pre-eclampsia detected using metabolomics and machine learning", Metabolomics, 1(3):227-234 (2005).
Kenny et al., "Detection and identification of Novel Metabolomic Biomarkers in Preeclampsia", Reprod Sci., 15 (6):591-597 (2008).
Kenny et al., "Robust Early Pregnancy Prediction of Later Preeclampsia Using Metabolomic Biomarkers.", Hypertension, 56(4):741-749 (2010).
Kudo et al. "Decreased tryptophan catabolism by placental indoleamine 2,3-dioxygenase in preeclampsia", Am J Obstet Gynecol. 188(3):719-726 (2003).
Lorentzen et al., "Fasting Serum Free Fatty Acids and Triglycerides are Increased Before 20 Weeks of Gestation in Women who Later Develop Preeclampsia", Hypertension in Pregnancy, 13(1):103-109 (1994).
Mills et al., "Prostacyclin and Thromboxane Changes Predating Clinical Onset of Preeclampsia: A Multicenter Prospective Study", JAMA. 282(4):356-362 (1999).

*Primary Examiner* — Michael Borin
(74) *Attorney, Agent, or Firm* — Nixon Peabody LLP

(57) ABSTRACT

A method for the early prediction of risk of hypertensive disorders in pregnant women, including for example eclampsia, mild pre-eclampsia, chronic hypertension, EPH gestosis, gestational hypertension, superimposed pre-eclampsia, HELLP syndrome, or nephropathy.

1 Claim, 9 Drawing Sheets

DETECTION OF RISK OF PRE-ECLAMPSIA

CROSS REFERENCE TO RELATED APPLICATIONS

This application is a 35 U.S.C. §371 National Phase Entry Application of International Application No. PCT/EP2010/070446 filed Dec. 21, 2010, which designates the U.S., and which claims benefit under 35 U.S.C. §119(e) of U.S. Provisional Application No. 61/288,465, filed Dec. 21, 2009, the contents of which are incorporated herein by reference in their entirety.

INTRODUCTION

The invention relates to a method of assessing the risk of a pregnant woman developing pre-eclampsia. In particular, the invention relates to a method for the early detection of a risk of pre-eclampsia developing in a pregnant woman.

Preeclampsia affects 5% of nulliparous pregnancies and globally afflicts approximately 4 million women annually. It remains a leading cause of maternal death throughout the world and is responsible for significant baby morbidity and mortality. Furthermore, preeclampsia has healthcare implications for the women later in life with an increased risk of hypertension, coronary artery disease, stroke and type 2 diabetes. Whilst the precise etiology of preeclampsia is unknown, accumulating evidence suggests that the disease results from a complex interaction between a poorly perfused placenta due to defective remodeling of the utero-placental arteries in early pregnancy and a maternal response to placental-derived triggers that involves the vasculature, along with inflammatory and coagulation processes linked to oxidative stress. Widespread plasma alterations precede the clinical onset of preeclampsia and there is intense interest in the identification of predictive biomarkers. Numerous candidate biomarkers have been proposed for prediction of disease including placental hormones, angiogenic factors and lipids. To date, none (nor any combination) has emerged with the requisite specificity and sensitivity to be of clinical use as a early predicting test for pre-eclampsia risk. Consequently, clinicians are unable to offer either targeted surveillance or potential preventative therapies to those nulliparous women at greatest risk.

It is an object of the invention to overcome at least one of the above-referenced problems.

STATEMENT OF INVENTION

The Applicant has identified a panel of metabolites that are associated with early prediction of risk of a pregnant woman developing pre-eclampsia, for example predicting risk of pre-eclampsia at about 11-17 weeks gestation. The panel of metabolites is shown in Table 1. The Applicant has shown that changes in the abundance (differential or modulated abundance) of one or more of the metabolites of Table 1, especially a metabolite selected from the group comprising 5-hydroxytryptophan, monosaccharide, decanoylcarnitine, methylglutaric acid and/or adipic acid, oleic acid, docosahexaenoic acid and/or docosatriynoic acid, γ-butyrolactone and/or oxolan-3-one, 2-oxovaleric acid and/or oxo-methylbutanoic acid, acetoacetic acid, hexadecenoyl-eicosatetraenoyl-sn-glycerol, sphingosine-1-phosphate, sphinganine-1-phosphate, and vitamin D3 derivatives (hereafter "Preferred Metabolites"), is associated with an increased risk of the woman subsequently developing (or having) pre-eclampsia. Thus, the invention relates to the use of one or more of the metabolites as a means of determining that a pregnant woman is at risk of developing pre-eclampsia at an early stage of pregnancy, prior to the development of conventional clinical symptoms, or aiding in the determination that a pregnant woman is at risk of developing pre-eclampsia. For most of the metabolites in Table 1, an elevated abundance of metabolite compared to a reference abundance (the abundance of the metabolite in a normal pregnancy, ie a negative control) correlates with an increased risk of development of pre-eclampsia, although for three of the metabolites, a decreased abundance compared to a reference abundance correlates with an increased risk of development of pre-eclampsia. It will be appreciated that a positive control may be employed as the reference, in which case for most of the metabolites in Table 1, a decreased abundance of metabolite compared to a reference abundance (the abundance of the metabolite in a pre-eclampsia pregnancy) correlates with an increased risk of development of pre-eclampsia, and for one of the metabolites, an increased abundance compared to a reference level correlates with an increased risk of development of pre-eclampsia.

TABLE 1

Table 1. Metabolites indentified in discovery and validation phases.

| METABOLITE | | AUCKLAND | | | | ADELAIDE | | | | Final |
|---|---|---|---|---|---|---|---|---|---|---|
| Identified as: | Metabolite Class | p-value | AU-ROC | Odd Ratio (95% CI) | up/down in PE? | p-value | AU-ROC | Odd Ratio (95% CI) | up/down in PE? | Rule ? |
| Isobutyrylglycine and/or N-Butyrylglycine | Acyl glycines | 0.05 | 0.64 | 2.0 (0.9-4.1) | up | | | | | |
| Taurine | Amino Acids | 0.01 | 0.65 | 3.4 (1.4-7.8) | up | | | | | |
| 5-Hydroxytryptophan | Amino Acids | 0.01 | 0.67 | 23.8 (3.0-187.3) | down | 0.833 | 0.61 | 2.4 (0.8, 7.1) | down | ✓ |
| Urea | Amino ketones | 0.01 | 0.66 | 2.9 (1.3-6.3) | down | 0.949 | 0.59 | 1.8 (0.8-4.5) | down | |
| 12-Ketodeoxycholic acid* | Bile acids | 0.02 | 0.67 | 2.6 (1.3-5.6) | up | 0.715 | 0.58 | 3.6 (0.9-14.4) | up | |
| Monosaccharide(s) | Carbohydrates | 0.01 | 0.71 | 6.1 (2.5-15.0) | up | 0.097 | 0.65 | 2.8 (1.1, 7.4) | up | ✓ |
| Sedoheptulose | Carbohydrates | 0.02 | 0.67 | 3.6 (1.5-8.4) | down | | | | | |
| Palmitoylcarnitine | Carnitines | 0.001 | 0.71 | 3.8 (1.7-8.2) | up | 0.244 | 0.63 | 3.4 (1.1, 10.6) | up | |
| Stearoylcarnitine | Carnitines | 0.006 | 0.69 | 3.3 | up | 0.610 | 0.61 | 2.7 | up | |

TABLE 1-continued

Table 1. Metabolites indentified in discovery and validation phases.

| METABOLITE | | AUCKLAND | | | | ADELAIDE | | | | Final Rule ? |
|---|---|---|---|---|---|---|---|---|---|---|
| Identified as: | Metabolite Class | p-value | AU-ROC | Odd Ratio (95% CI) | up/down in PE? | p-value | AU-ROC | Odd Ratio (95% CI) | up/down in PE? | |
| Decanoylcarnitine | Carnitines | 0.007 | 0.68 | 3.1 (1.5-7.4) (1.4-6.9) | up | 0.624 | 0.59 | 1.6 (1.0, 7.5) (0.4-6.1) | up | ✓ |
| Octanoylcarnitine | Carnitines | 0.01 | 0.7 | 3.0 (1.4-6.5) | up | 0.494 | 0.61 | 1.9 (0.7-5.3) | up | |
| Acetylcarnitine | Carnitines | 0.02 | 0.66 | 2.3 (1.1-5.0) | up | 0.207 | 0.65 | 4.7 (1.2-18.3) | up | |
| Dodecanoylcarnitine | Carnitines | 0.05 | 0.69 | 3.2 (1.2-8.8) | up | 0.349 | 0.63 | 4.6 (0.9-23.5) | up | |
| Methylglutaric acid and/or adipic acid* | Dicarboxylic acid | 0.01 | 0.64 | 2.6 (1.2-5.9) | down | 0.010 | 0.72 | 3.8 (1.4-10.0) | down | ✓ |
| 8,11,14-Eicosatrienoic acid | Eicosanoids | 0.003 | 0.64 | 8.7 (2.5-29.9) | up | 0.144 | 0.64 | 2.1 (0.8-5.3) | up | |
| 20-Carboxyleukotriene B4 | Eicosanoids | 0.005 | 0.69 | 3.1 (1.5-6.6) | up | 0.268 | 0.64 | 2.1 (0.8-5.0) | up | |
| Eicosapentaenoic acid and/or retinoic acid | Eicosanoids and/or retinoids | 0.03 | 0.61 | 3.2 (1.3-7.7) | up | | | | | |
| Isovaleric acid and/or Valeric acid | Fatty Acids | 0.007 | 0.68 | 3.8 (1.7-8.6) | up | | | | | |
| Oleic acid | Fatty Acids | 0.007 | 0.68 | 3.1 (1.4-6.7) | up | 0.276 | 0.63 | 2.0 (0.8-4.8) | up | ✓ |
| Linoleic acid | Fatty Acids | 0.01 | 0.66 | 3.5 (1.6-7.9) | up | 0.441 | 0.60 | 2.3 (0.8-6.5) | up | |
| Docosahexaenoic acid and/or docosatriynoic acid | Fatty Acids | 0.01 | 0.66 | 5.6 (1.9-16.3) | up | 0.204 | 0.65 | 2.8 (1.0-8.0) | up | ✓ |
| Hydroxy-octadecenoic acid and/or oxo-octadecanoic acid | Fatty Acids | 0.01 | 0.66 | 3.5 (1.4-8.4) | up | 0.498 | 0.58 | 2.0 (0.6-6.6) | up | |
| Hexadecanoic acid | Fatty Acids | 0.02 | 0.67 | 7.5 (2.1-27.3) | up | 0.317 | 0.62 | 2.0 (0.8-5.2) | up | |
| Eicosatetraenoic acid | Fatty Acids | 0.02 | 0.67 | 3.1 (1.4-7.1) | up | 0.244 | 0.63 | 4.1 (1.0-16.3) | up | |
| Octadecanoic acid | Fatty Acids | 0.02 | 0.67 | 3.0 (1.4-6.5) | up | 0.133 | 0.64 | 2.1 (0.8-5.3) | up | |
| Docosahexaenoic acid | Fatty Acids | 0.02 | 0.67 | 2.6 (1.2-5.9) | up | | | | | |
| γ-Butyrolactone and/or Oxolan-3-one | Fatty acids and/or ketones | 0.0004 | 0.72 | 4.3 (1.8-10.0) | up | 0.513 | 0.60 | 1.6 (0.6-4.1) | up | ✓ |
| 2-Oxovaleric acid and/or oxo-methylbutanoic acid | Fatty Acids or keto acids | 0.03 | 0.66 | 2.6 (1.2-5.4) | up | 0.010 | 0.72 | 4.7 (1.8-12.3) | up | ✓ |
| 3-hydroxybutanoic acid and/or 2-hydroxybutanoic acid | Keto or Hydroxy FA | 0.002 | 0.71 | 5.1 (1.9-13.8) | up | 0.459 | 0.61 | 1.8 (0.7-4.7) | up | |
| Oxo-tetradecanoic acid and/or hydroxytetradecenoic acid* | Keto or Hydroxy FA | 0.006 | 0.72 | 3.6 (1.5-8.8) | up | | | | | |
| Acetoacetic acid | Keto or Hydroxy FA | 0.01 | 0.67 | 2.9 (1.3-6.4) | up | 0.069 | 0.70 | 4.2 (1.6-11.1) | up | ✓ |
| Oxoheptanoic acid | Keto or Hydroxy FA | 0.02 | 0.66 | 2.4 (1.1-5.3) | up | | | | | |
| Di-(heptadecadienoyl)-eicosanoyl-sn-glycerol* | Lipids | 0.002 | 0.66 | 3.5 (1.5-8.0) | down | 0.170 | 0.65 | 2.78 (1.2-6.9) | down | |
| Hexadecenoyl-eicosatetraenoyl-sn-glycerol* | Lipids | 0.01 | 0.69 | 3.0 (1.4-6.9) | up | 0.035 | 0.69 | 2.8 (1.1-6.9) | up | ✓ |
| Di-(octadecadienoyl)-sn-glycerol* | Lipids | 0.05 | 0.65 | 2.2 (1.0-4.5) | up | 0.007 | 0.73 | 5.6 (2.1-14.6) | up | ✓ |
| Octadecenoyl-hexadecanoyl-sn-glycero-3-phosphoserine* | Phosphatidylserines | 0.01 | 0.64 | 3.6 (1.4-9.0) | down | 0.883 | 0.58 | 1.7 (0.7-4.1) | down | |
| Octadecenoyl-sn-glycero-3-phosphoserine* | Phosphatidylserines | 0.02 | 0.65 | 2.8 (1.2-6.1) | up | 0.494 | 0.61 | 1.9 (0.8-4.6) | up | |
| Dioctanoyl-sn-glycero-3-phosphocholine* | Phospholipids | 0.01 | 0.67 | 3.0 (1.4-6.3) | up | 0.605 | 0.60 | 2.5 (0.9-7.2) | up | |
| Sphingosine 1-phosphate | Phospholipids | 0.01 | 0.68 | 3.3 (1.5-7.2) | up | 0.037 | 0.69 | 4.2 (1.6-11.1) | up | ✓ |
| Sphinganine 1-phosphate | Phospholipids | 0.03 | 0.66 | 2.6 (1.3-5.6) | up | 0.939 | 0.59 | 1.8 (0.7-4.5) | up | ✓ |

TABLE 1-continued

Table 1. Metabolites indentified in discovery and validation phases.

| | | AUCKLAND | | | | ADELAIDE | | | | Final |
| METABOLITE | | | AU- | Odd Ratio | up/down | | AU- | Odd Ratio | up/down | Rule |
| Identified as: | Metabolite Class | p-value | ROC | (95% CI) | in PE? | p-value | ROC | (95% CI) | in PE? | ? |
|---|---|---|---|---|---|---|---|---|---|---|
| Bilirubin | Porphyrins | 0.006 | 0.68 | 3.2 (1.5-6.9) | up | | | | | |
| Biliverdin | Porphyrins | 0.01 | 0.67 | 3.1 (1.4-6.8) | up | | | | | |
| Heme | Porphyrins | 0.02 | 0.63 | 2.9 (1.3-6.8) | up | | | | | |
| Vitamin D3 derivatives | Steroids or Steroid Derivatives | 0.002 | 0.69 | 6.2 (2.3-16.4) | up | 0.153 | 0.63 | 2.8 (1.0-7.4) | up | ✓ |
| Steroid and/or Etiocholan-3-alpha-o17-one 3-glucuronide* | Steroids or Steroid Derivatives | 0.01 | 0.68 | 2.5 (1.2-5.2) | up | 0.979 | 0.58 | 1.4 (0.6-3.5) | up | |

*metabolite identification included other similar metabolites of the same class.

According to the invention, there is provided a method of, or assay for, predicting the risk, or aiding in the prediction of risk, of a pregnant woman developing (or having) pre-eclampsia comprising a step of assaying a biological sample from the woman to determine an abundance of at least one metabolite biomarker selected from the group shown in Table 1, especially the group comprising 5-hydroxytryptophan, monosaccharide, decanoylcarnitine, methylglutaric acid and/or adipic acid, oleic acid, docosahexaenoic acid and/or docosatriynoic acid, γ-butyrolactone and/or oxolan-3-one, 2-oxovaleric acid and/or oxo-methylbutanoic acid, acetoacetic acid, hexadecenoyl-eicosatetraenoyl-sn-glycerol, sphingosine-1-phosphate, sphinganine-1-phosphate, and vitamin D3 derivatives (Preferred Metabolites), wherein a modulated abundance of the at least one metabolite biomarker relative to a reference abundance for that biomarker correlates with a risk of the woman developing (or having) pre-eclampsia. Preferably, the method is a method for the early prediction of risk (or early detection) of pre-eclampsia, in which the biological sample is obtained from the pregnant woman at 11 to 19 weeks, preferably from 11 to 18 weeks, more preferably from 11 to 17 weeks, and ideally at about 15+/−1 or 2 weeks, gestation. Ideally, the reference abundance for the metabolite biomarker is obtained from a reference biological sample (or samples, for example pooled samples) obtained from a pregnant woman at the same gestational period in weeks (+/−one or two weeks) as the test biological sample.

In one aspect, the reference abundance is the abundance of the metabolite marker in a biological sample obtained from a subject who had a non-eventful pregnancy. The non-eventful pregnancy may be a pregnancy without pre-eclampsia, or a pregnancy without pre-eclampsia and without any other complications. Ideally, the subject in an age matched, ideally nulliparous, subject who had a non-eventful pregnancy, and the biological sample is ideally obtained from the subject at the same gestational period as the test subject +/−4 weeks, 3 weeks, 2 weeks, or 1 week. Thus, a reference abundance may be obtained from a biological sample obtained from a subject at 11 to 19 weeks, preferably from 12 to 18 weeks, more preferably from 13 to 17 weeks, and ideally at about 15+/−1 week, gestation. In another embodiment, the reference abundance may be obtained from a biological sample obtained from a subject who had pre-eclampsia, the biological sample being ideally obtained from the subject at the same gestational period as the test subject +/−4 weeks, +/−3 weeks, +/−2 weeks, or +/−1 week. In this case, modulated abundance would predict, or aid in the prediction, of non-occurance of pre-eclampsia (i.e. a normotensive pregnancy). For any of the metabolite markers, methods of detection of modulated abundance are described below. Thus, for example, when UPLC-MS is employed as means of detecting modulated abundance, the critical p-value for clinical significance is ideally set at 0.05.

Thus, in one aspect, the invention preferably involves assaying a biological sample from a test patient to determine an abundance of a metabolite selected from Table 1, and ideally at least two metabolites from Table 1, and determining whether the abundance of the or each metabolite is modulated relative to a reference abundance, wherein a modulated abundance of the metabolite correlates with an increased risk of pre-eclampsia. Ideally, the or each metabolite is selected from the group of Preferred Metabolites.

Pre-eclampsia affects 5% of nulliparous pregnancies and globally afflicts approximately 4 million women annually. Clinical symptoms of pre-eclampsia generally do not appear before 20 weeks gestation, and it is desirable to detect (or predict) pre-eclampsia, or risk of pre-eclampsia, as early as possible to allow for early intervention. The metabolite biomarkers of the invention can predict, or aid in the prediction, of pre-eclampsia at an early gestational stage, for example prior to the appearance of clinical symptoms.

Thus, in one embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of 5-hydroxytryptophan, wherein a modulated abundance of 5-hydroxytryptiophan relative to a reference abundance of hydroxytryptophan correlates with an increased risk of development of pre-eclampsia. Modulated abundance of 5-hydroxytryptophan has a predictive power (in the form of an Odds Ratio (95% cI)) of 23.8. Thus, detection of a modulated abundance of 5-hydroxytryptophan predicts an increased risk of pre-eclampsia prior to the onset of clinical symptoms. When the reference abundance is from a subject who did not develop pre-eclampsia, decreased abundance indicates risk. However, when the reference abundance is from a subject who did develop pre-eclampsia, elevated abundance indicates risk.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of monosaccharide (typically including sedoheptulose), wherein a modulated abundance of monosaccharide relative to a reference abundance of monosaccharide correlates with an increased risk of development of pre-eclampsia. Modulated abundance of monosaccharide has a predictive power (in the form of an Odds Ratio (95% cl)) of 6.1. Thus, detection of a modulated abundance of monosaccharide predicts an increased risk of pre-eclampsia prior to the onset of clinical symptoms. When the reference abundance is from a subject who did not develop pre-eclampsia, increased abundance relative to the reference indicates risk. However, when the reference abundance is from a subject who did develop pre-eclampsia, decreased abundance relative to the reference indicates risk. In the case of monosaccharides, the abundance of total monosaccharides in the sample is suitably determined.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of decanoylcarnitine, wherein a modulated abundance of decanoylcarnitine relative to a reference abundance of decanoylcarnitine correlates with an increased risk of development of pre-eclampsia. Modulated abundance of decanoylcarnitine has a predictive power (in the form of an Odds Ratio (95% cl)) of 3.1. Thus, detection of a modulated abundance of decanoylcarnitine predicts an increased risk of pre-eclampsia prior to the onset of clinical symptoms. When the reference abundance is from a subject who did not develop pre-eclampsia, increased abundance relative to the reference indicates risk. However, when the reference abundance is from a subject who did develop pre-eclampsia, decreased abundance relative to the reference indicates risk.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of methylglutaric acid, adipic acid, or methylglutaric acid and adipic acid, wherein a modulated abundance of methylglutaric acid, adipic acid, or methylglutaric acid and adipic acid relative to a reference abundance of methylglutaric acid, adipic acid, or methylglutaric acid and adipic acid, respectively, correlates with an increased risk of development of pre-eclampsia. Modulated abundance of methylglutaric acid, adipic acid, or methylglutaric acid and adipic acid, has a predictive power (in the form of an Odds Ratio (95% cl)) of 2.6. Thus, detection of a modulated abundance of methylglutaric acid, adipic acid, or methylglutaric acid and adipic acid, predicts an increased risk of pre-eclampsia prior to the onset of clinical symptoms. When the reference abundance is from a subject who did not develop pre-eclampsia, decreased abundance relative to the reference indicates risk. However, when the reference abundance is from a subject who did develop pre-eclampsia, increased abundance relative to the reference indicates risk.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of oleic acid, wherein a modulated abundance of oleic acid relative to a reference abundance of oleic acid correlates with an increased risk of development of pre-eclampsia. Modulated abundance of oleic acid has a predictive power (in the form of an Odds Ratio (95% cl)) of 3.1. Thus, detection of a modulated abundance of oleic acid predicts an increased risk of pre-eclampsia prior to the onset of clinical symptoms. When the reference abundance is from a subject who did not develop pre-eclampsia, increased abundance relative to the reference indicates risk. However, when the reference abundance is from a subject who did develop pre-eclampsia, decreased abundance relative to the reference indicates risk.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of docosahexaenoic acid, docosatriynoic acid, or docosahexaenoic acid and docosatriynoic acid, wherein a modulated abundance of docosahexaenoic acid, docosatriynoic acid, or docosahexaenoic acid and docosatriynoic acid relative to a reference abundance of docosahexaenoic acid, docosatriynoic acid, or docosahexaenoic acid and docosatriynoic acid, respectively, correlates with an increased risk of development of pre-eclampsia. Modulated abundance of docosahexaenoic acid, docosatriynoic acid, or docosahexaenoic acid and docosatriynoic acid, has a predictive power (in the form of an Odds Ratio (95% cl)) of 5.6. Thus, detection of a modulated abundance of docosahexaenoic acid, docosatriynoic acid, or docosahexaenoic acid and docosatriynoic acid, predicts an increased risk of pre-eclampsia prior to the onset of clinical symptoms. When the reference abundance is from a subject who did not develop pre-eclampsia, increased abundance relative to the reference indicates risk. However, when the reference abundance is from a subject who did develop pre-eclampsia, decreased abundance relative to the reference indicates risk.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of γ-butyrolactone, oxolan-3-one, or γ-butyrolactone and oxolan-3-one, wherein a modulated abundance of γ-butyrolactone, oxolan-3-one, or γ-butyrolactone and oxolan-3-one relative to a reference abundance of γ-butyrolactone, oxolan-3-one, or γ-butyrolactone and oxolan-3-one, respectively, correlates with an increased risk of development of pre-eclampsia. Modulated abundance of γ-butyrolactone, oxolan-3-one, or γ-butyrolactone and oxolan-3-one has a predictive power (in the form of an Odds Ratio (95% cl)) of 4.3. Thus, detection of a modulated abundance of γ-butyrolactone, oxolan-3-one, or γ-butyrolactone and oxolan-3-one, predicts an increased risk of pre-eclampsia prior to the onset of clinical symptoms. When the reference abundance is from a subject who did not develop pre-eclampsia, increased abundance relative to the reference indicates risk. However, when the reference abundance is from a subject who did develop pre-eclampsia, decreased abundance relative to the reference indicates risk.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of 2-oxovaleric acid, oxomethylbutanoic acid, or 2-oxovaleric acid and oxomethylbutanoic acid, wherein a modulated abundance of 2-oxovaleric acid, oxomethylbutanoic acid, or 2-oxovaleric acid and oxomethylbutanoic acid, relative to a reference abundance of 2-oxovaleric acid, oxomethylbutanoic acid, or 2-oxovaleric acid and oxomethylbutanoic acid, respectively, correlates with an increased risk of development of pre-eclampsia. Modulated abundance of 2-oxovaleric acid, oxomethylbutanoic acid, or 2-oxovaleric acid and oxomethylbutanoic acid, has a predictive power (in the form of an Odds Ratio (95% cl)) of 2.6. Thus, detection of a modulated abundance of 2-oxovaleric acid, oxomethylbutanoic acid, or 2-oxovaleric acid and oxomethylbutanoic acid, predicts an increased risk of pre-eclampsia prior to the onset of clinical symptoms. When the reference abundance is from a subject who did not develop pre-eclampsia, increased abundance relative to the reference indicates risk. However, when the reference abundance is from a subject who did develop pre-eclampsia, decreased abundance relative to the reference indicates risk.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of acetoacetic acid, wherein a modulated abundance of acetoacetic acid relative to a reference abundance of acetoacetic acid correlates with an increased risk of development of pre-eclampsia. Modulated abundance of acetoacetic acid has a predictive power (in the form of an Odds Ratio (95% cl)) of 2.9. Thus, detection of a modulated abundance of acetoacetic acid predicts an increased risk of pre-eclampsia prior to the onset of clinical symptoms. When the reference abundance is from a subject who did not develop pre-eclampsia, increased abundance relative to the reference indicates risk. However, when the reference abundance is from a subject who did develop pre-eclampsia, decreased abundance relative to the reference indicates risk.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of hexadecenoyl-eicosatetraenoyl-sn-glycerol, wherein a modulated abundance of hexadecenoyl-eicosatetraenoyl-sn-glycerol relative to a reference abundance of hexadecenoyl-eicosatetraenoyl-sn-glycerol correlates with an increased risk of development of pre-eclampsia. Modulated abundance of hexadecenoyl-eicosatetraenoyl-sn-glycerol has a predictive power (in the form of an Odds Ratio (95% cl)) of 3.0. Thus, detection of a modulated abundance of hexadecenoyl-eicosatetraenoyl-sn-glycerol predicts an increased risk of pre-eclampsia prior to the onset of clinical symptoms. When the reference abundance is from a subject who did not develop pre-eclampsia, increased abundance relative to the reference indicates risk. However, when the reference abundance is from a subject who did develop pre-eclampsia, decreased abundance relative to the reference indicates risk.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of sphingosine-1-phosphate, wherein a modulated abundance of sphingosine-1-phosphate relative to a reference abundance of sphingosine-1-phosphate correlates with an increased risk of development of pre-eclampsia. Modulated abundance of sphingosine-1-phosphate has a predictive power (in the form of an Odds Ratio (95% cl)) of 3.3. Thus, detection of a modulated abundance of sphingosine-1-phosphate predicts an increased risk of pre-eclampsia prior to the onset of clinical symptoms. When the reference abundance is from a subject who did not develop pre-eclampsia, increased abundance relative to the reference indicates risk. However, when the reference abundance is from a subject who did develop pre-eclampsia, decreased abundance relative to the reference indicates risk.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of sphinganine-1-phosphate, wherein a modulated abundance of sphinganine-1-phosphate relative to a reference abundance of sphinganine-1-phosphate correlates with an increased risk of development of pre-eclampsia. Modulated abundance of sphinganine-1-phosphate has a predictive power (in the form of an Odds Ratio (95% cl)) of 2.6. Thus, detection of a modulated abundance of sphinganine-1-phosphate predicts an increased risk of pre-eclampsia prior to the onset of clinical symptoms. When the reference abundance is from a subject who did not develop pre-eclampsia, increased abundance relative to the reference indicates risk. However, when the reference abundance is from a subject who did develop pre-eclampsia, decreased abundance relative to the reference indicates risk.

In another embodiment, the invention relates to a method of determining, or aiding in the determination, ideally at an early stage of the pregnancy, that a pregnant woman is at risk of developing (or has developed) pre-eclampsia, which method comprises a step of assaying a biological sample typically obtained from the woman at 11 to 17 weeks gestation to determine an abundance of vitamin D3 derivatives, wherein a modulated abundance of vitamin D3 derivatives relative to a reference abundance of vitamin D3 derivatives correlates with an increased risk of development of pre-eclampsia. Modulated abundance of vitamin D3 derivatives has a predictive power (in the form of an Odds Ratio (95% cl)) of 6.2. Thus, detection of a modulated abundance of vitamin D3 derivatives predicts an increased risk of pre-eclampsia prior to the onset of clinical symptoms. When the reference abundance is from a subject who did not develop pre-eclampsia, increased abundance relative to the reference indicates risk. However, when the reference abundance is from a subject who did develop pre-eclampsia, decreased abundance relative to the reference indicates risk. In the case of vitamin D3 derivatives, the abundance of total vitamin D3 derivatives in the sample is suitably determined (i.e. 25-hydroxy vitamin D3, 1,25-dihydroxy vitamin D3, and 24,25-dihydroxy vitamin D3).

It will be appreciated that each of the biomarkers of Table 1 may be employed to inform risk of a pregnant woman developing pre-eclampsia. Where multiple biomarkers are employed in the method or assay of the invention, modulated abundance of one of the biomarkers indicates an increased risk of the presence of, or development of, pre-eclampsia. Modulated abundance of two, three, four biomarkers indicates increasingly higher risk of development of, or presence of, pre-eclampsia. The methods of the invention may also employ maternal clinical parameters in combination with one or more of the biomarkers of Table 1 to inform on risk. Suitable clinical parameters (clinical risk variables) include one or more of blood pressure, body mass index (BMI), and age, although other clinical parameters may be employed. Thus, in a preferred embodiment, the method of the invention comprises a step of predicting risk (or aiding in the prediction of risk) of a woman developing pre-eclampsia which employs a step of detecting modulated abundance of a metabolite biomarker of Table 1, especially a metabolite selected from the Preferred Metabolites, relative to a reference abundance to provide a predictive risk value, and obtaining at least one clinical risk variable from the woman, typically selected from blood pressure, BMI and age, and correlating the predictive risk value and the at least one clinical risk variable with overall risk of pre-eclampsia. Preferably, at least two clinical risk variables are obtained from the woman (for example blood pressure and age, or blood pressure and BMI, or age and BMI), wherein the predictive risk value and the at least two clinical risk variables are correlated with overall risk of pre-eclampsia. Ideally, at least three clinical risk variables are obtained from the woman (for example blood pressure, age and BMI), wherein the predictive risk value and the at least three clinical risk variables are correlated with overall risk of pre-eclampsia.

It will also be appreciated that combinations of biomarkers may be employed to increase the predictive power of the methods of the invention. Thus, in a preferred embodiment of the invention, the abundance of at least 2, 3, 4, 5, 6, 7, 8, 9, 10, 11, 12 or 13 of the metabolite classes of Table 1 is determined. In the context of the invention, the rows of Table 1 designates the metabolite classes—thus, methylglutaric acid and/or adipic acid are considered to be one metabolite class. Thus, the method of the invention ideally involves determining the abundance of substantially all, or all, of the following 13 metabolites (Preferred Metabolites): 5-hydroxytryptophan; monosaccharide; decanoylcarnitine; methylglutaric acid and/or adipic acid; oleic acid; docosahexaenoic acid and/or docosatriynoic acid; γ-butyrolactone and/or oxolan-3-one; 2-oxovaleric acid and/or oxo-methylbutanoic acid; acetoacetic acid; hexadecenoyl-eicosatetraenoyl-sn-glycerol; sphingosine-1-phosphate; sphinganine-1-phosphate; and vitamin D3 derivatives. The term "substantially all" should be understood to mean at least 10, 11, 12, or 13 of the metabolites. Where a metabolite is indicated as "A and/or B" (for example, γ-Butyrolactone and/or Oxolan-3-one), it is considered herein as a single metabolite, and abundance for that metabolite means the abundance of one, the other, or the sum of the abundance of the two metabolites. Ideally, the method of the invention comprises determining the abundance of all 13 of the metabolites recited above.

The method of the invention is ideally suited to the early detection of risk of pre-eclampsia. This enables early clinical intervention to manage the course of the disease and avoid poor outcome. Thus, a biological sample may be obtained from the test subject at about 15 weeks gestation, and then analysed for metabolite abundance. Generally, the biological sample is blood, or is derived from blood, for example serum. Methods for determining abundance of metabolites will be known to those skilled in the field and may include, for example, liquid chromatography and mass spectrometry to generate metabolite-associated peaks. Relative abundance may be determined by comparing these peaks with corresponding peaks from a reference sample. For a metabolite class that includes two metabolites, relative abundance is determined by comparing the sum of the two metabolite peaks with the sum of the peaks for the metabolites from a reference sample, or by comparing one of the metabolite peaks with a reference metabolite peak. Methods for determining whether the relative abundance is significant in the context of the present invention are described below.

Thus, in a preferred embodiment, the invention provides a method for providing an early estimation of the risk of pre-eclampsia comprising the steps of assaying a plasma sample obtained from the patient at up to 17 weeks gestation for an adundance of a plurality of metabolite biomarkers including 5-hydroxytryptophan, monosaccharide, decanoylcarnitine, methylglutaric acid and/or adipic acid, oleic acid, docosahexaenoic acid and/or docosatriynoic acid, γ-butyrolactone and/or oxolan-3-one, 2-oxovaleric acid and/or oxo-methylbutanoic acid, acetoacetic acid, hexadecenoyl-eicosatetraenoyl-sn-glycerol, sphingosine-1-phosphate, sphinganine-1-phosphate, and vitamin D3 derivatives, and correlating the determined abundance for each biomarker with a reference abundance. Thus, for example, where the abundance of substantially all of the metabolites (ie 10, 11, 12, or 13) is modulated compared to a reference abundance for each metabolite, this correlates with a high risk of pre-eclampsia. Conversely, where the abundance of none of the metabolite classes (ie 0, 1, 2, or 3) is modulated, this correlates with a no increased risk of pre-eclampsia. When modulated abundance of all of the above-referenced metabolites is detected, this correlates with an Odds Ratio of at least 16.4 (95% CI 7-40), indicating that is it far more likely that the patient will develop pre-eclampsia than not develop pre-eclampsia.

In one embodiment of the invention, the method involves determining modulated abundance of a panel of metabolite classes, especially a panel selected from Table 1. In one embodiment, the panel comprises at least one amino acid, at least one carbohydrate, at least one carnitine, at least one diacrboxylic acid, at least one fatty acid and/or ketone, at least one fatty acid and/or keto acid, optionally at least one ketone, at least one lipid, at least one phospholipid, at least one keto or fatty acid, and at least one steroid or steroid derivative. Suitably, the amino acid is 5-hydroxytryptophan or taurine. Suitably, the carbohydrate is a monosaccharide or a sedoheptulose. Suitably, the carnitine is selected from palmitoylcarnitine, stearoylcarnitine, decanoylcarnitine, octanolycarnitine, acetylcarnitine, and dodecanoylcarnitine. Suitably, the dicarboxylic acid is methylglutaric acid and/or adipic acid. Suitably, the fatty acid is selected from isovaleric acid and/or valeric acid, oleic acid, linoleic acid, docosahexenoic acid and/or docosatriynoic acid, hydroxyl-oxctadecanoic acid and/or oxo-actadecanoic acid, hexadecanoic acid, eicosatetraenoic acid, octadecanoic acid, and docosahexaenoic acid. Suitably the fatty acid and/or ketone is selected from γ-butyrolactone and/or oxolan-3-one. Suitably, the fatty acid or keto acid is selected from 2-oxovaleric acid and/or oxo-methylbutanoic acid. Suitably the keto or hydroxy fatty acid is selected from 3-hydroxybutanoic acid or 2-hydroxybutanoic acid, oxo-tetradecanoic acid and/or hydroxytetradecenoic acid, acetoacetic acid, and oxoheptanoic acid. Suitably the lipid is selected from di-(heptadecadienoyl)-eicosanoyl-sn-glycerol, hexadecenoyl-eicosatetraenoyl-sn-glycerol, and di-(octadecdienoyl)-sn-glycerol. Suitably, the phospholipid is selected from dioctanoyl-sn-glycero-3-phosphocholine, sphingosine 1-phosphate, and sphinganine 1-phosphate. Suitably, the steroid or steroid derivative is selected from Vitamin D3 derivatives, and steroid and/or Etiocholan-3-alpha-o17-one 3-glucuronide.

Typically, the method involves determining an abundance of a panel of at least two metabolites classes relative to a reference value for each respective metabolite, and correlating the abundance of the metabolite classes with risk of development of pre-eclampsia. Suitably, the panel of metabolite classes comprises 5-HT or S1P or 5-HT and S1P. In one embodiment, the panel of metabolite classes comprise S1P and/or 5-HT in combination with docosahecaenoic acid and/or docosatriynoic acid and/or oleic acid. Ideally, the panel of metabolite classes comprises 5-HT, S1P, docosahecaenoic acid and/or docosatriynoic acid, and oleic acid, optionally in combination with at least one, two, three, four, five or six of the remaining metabolites of Table 1.

In a preferred embodiment of the invention, the method is a method for early detection of risk of pre-eclampsia. The term "early detection" as employed herein should be understood to mean detection of risk at 11 to 19 weeks, 11 to 18 weeks, 11 to 17 weeks, 11 to 16 weeks, or 11 to 15 weeks gestation, and preferably 12 to 17 weeks, 13 to 16 weeks, and ideally about 15+/−one or two weeks gestation.

The biological sample (for the test sample or the control) may be any biological fluid obtained from the subject or the fetus, including blood, serum, saliva, amniotic fluid, cerebrospinal fluid. Ideally, the biological sample is serum. The subject may be fasting or non-fasting when the biological sample is obtained.

In one embodiment of the invention, the abundance of the at least one metabolite or metabolite class (relative to a reference value) is determined using relative quantification using for example mass spectrometry or chromatography, typically liquid chromatography. Thus, the abundance value assigned to any given metabolite may be provided in terms of a relative abundance (relative to a reference abundance, for example from a normal pregnanacy or a reference abundance for a pre-eclamptic pregnancy). In one particularly preferred embodiment of the invention, relative abundance of a metabolite or metabolite class may be determined using mass spectrometry in which the sample is optionally run in tandem with a reference sample. Ideally, the mass spectrometry is time-of-flight mass spectrometry or ultra performance liquid chromatography-mass spectrometry. In another embodiment of the invention, relative abundance of a metabolite or metabolite class may be determined using high performance liquid chromatography in which the sample is optionally run in tandem with a reference sample.

In one aspect, the invention relates to a method for the early detection of a risk of pre-eclampsia developing in a pregnant woman comprising the steps of assaying a biological sample, generally blood or a blood-derived product such as serum, obtained from the pregnant woman at from 4 and 25 weeks gestation for an abundance of a metabolite selected from Table 1 (ideally one or more Preferred Metabolites) relative to a reference abundance for the metabolite, wherein a modulated abundance of the metabolite relative to the reference abundance correlates with a risk of the woman developing pre-eclampsia.

Suitably, modulated abundance is determined using mass spectrometry in which the test sample is optionally run in tandem with a reference sample obtained at or about the same gestational stage (for example +/−5 weeks, +/−4 weeks, +/−3 weeks, +/−2 weeks, and ideally +/−one week) as the test sample and obtained from a pregnant woman who has a normal pregnancy outcome (negative control) or a pregnant woman who has a pre-eclamptic pregnancy (positive control). Alternatively, the mass spectrometer may be pre-set with reference abundance values for the or each metabolite whereby for the or each metabolite the machine is set to detect modulated relative abundance.

In one embodiment of the invention, the method of the invention involves an additional step of determining one or more further characteristics of the pregnant woman, including blood pressure, age, urine protein concentration, smoker status, maternal age, Body Mass Index, family history of preeclampsia or coronary vascular disease and ultrasound parameters including measurements of fetal biometry and umbilical and uterine artery Doppler waveform analysis.

The invention may be primarily employed as a means of assessment of the risk, or aiding in the assessment of the risk, that a pregnant woman will develop pre-eclampsia. However, the invention may also be employed as a means of diagnosing the presence of pre-eclampsia, predicting the risk of pre-eclampsia, assessment of likely patient outcome due to the syndrome, and assessment of effectiveness of a treatment for pre-eclampsia in which the levels of one or more of the metabolite markers of the invention assessed over a period of treatment to monitor for effectiveness of the treatment. In terms of prediction, the methods of the invention typically provides for a detection rate of at least 50%, 60% or 70% in which the false positive rate is at most 20% when all metabolite classes are employed. Further, the methods of the invention typically provides for a detection rate of at least 70%, 80% or 90% in which the false positive rate is at most 40% when all metabolite classes are employed.

In one embodiment of the invention, the method is a method of monitoring the effectiveness of a treatment for a pre-eclampsia, in which changes in the abundance of a metabolite or a plurality of metabolites selected from the metabolites of Table 1 is correlated with effectiveness of the treatment. For example, when the metabolite being assayed is a metabolite selected from the group of Table 1 (excluding the dicarboxylic acids and 5-hydroxytryptophan), then a decrease in abundance of the metabolite is generally indicative of effectiveness of the treatment. Generally, the method will involve an initial assay to determine the starting abundance level of the or each metabolite, and then further periodic measurements of the abundance level of the or each metabolite during and/or after the course of the treatment to monitor abundance levels of the or each marker. Likewise, when the metabolite being assayed is 5-hydroxytryptophan or one of the dicarboxylic acids of Table 1, then a decrease in abundance of the metabolite is generally indicative of effectiveness of the treatment. Generally, the method will involve an initial assay to determine the starting abundance level of the or each metabolite, and then further periodic measurements of the abundance level of the or each metabolite during and/or after the course of the treatment to monitor abundance levels of the or each marker.

Preferably, the step of determining the quantitative estimate of pre-eclampsia risk comprises determining the likelihood of pre-eclampsia using a multivariate analysis which typically comprises using the abundance of the or each metabolite biomarker and distribution parameters derived from a set of reference abundance values. Ideally, the multivariate analysis employs a multivariate discriminant PLS-DA model or a multivariate discriminant PC-CVA model.

The methods of the invention relate to the early prediction of pre-eclampsia. However, the methods of the invention are also applicable for the early prediction of risk of hypertensive disorders in pregnant women, including for example eclampsia, mild pre-eclampsia, chronic hypertension, EPH gestosis, gestational hypertension, superimposed pre-eclampsia, HELLP syndrome, or nephropathy. Further, while the invention is described with reference to pregnant humans, it is also applicable to pregnant higher mammals.

The invention also relates to a method of prevention or treatment of pre-eclampsia in a pregnant woman comprising a step of employing the methods or assays of the invention to identify risk of development, or diagnose the presence, of pre-eclampsia in a pregnant woman, and applying clinical intervention to a woman who is identified as being at increased risk of developing, or who is diagnosed with, pre-eclampsia. Treatment may include controlling blood pressure, for example by administering an anti-hypertensive medicament (for example, a rennin inhibitor, an angiotensin-2 receptor blocker, an ACE inhibitor), dietary intervention, or the like.

DETAILED DESCRIPTION OF THE INVENTION

The invention is generally based on the finding that the levels of certain metabolites are associated with pre-eclampsia, and that these metabolites may therefore function as diagnostic and/or prognostic variables of pre-eclampsia, typically at an early gestation stage. The data presented herein shows that the abundance of these biomarkers change at an early stage in the development of the syndrome, earlier than the normal symptoms of pre-eclampsia appear, and the biomarkers can therefore function as prognostic variables of pre-eclampsia risk enabling early detection of the syndrome. This is especially important as the morbidity and mortality associated with pre-eclampsia increases the later the syndrome is detected. The present invention therefore provides a means for early detection of pre-eclampsia allowing earlier clinical intervention and therefore improved outcome.

Systems

Embodiments of the invention also provide for systems (and computer readable media for causing computer systems) to perform a method for detecting and/or identifying that a pregnant woman is at risk of developing pre-eclampsia.

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

Figure 8:
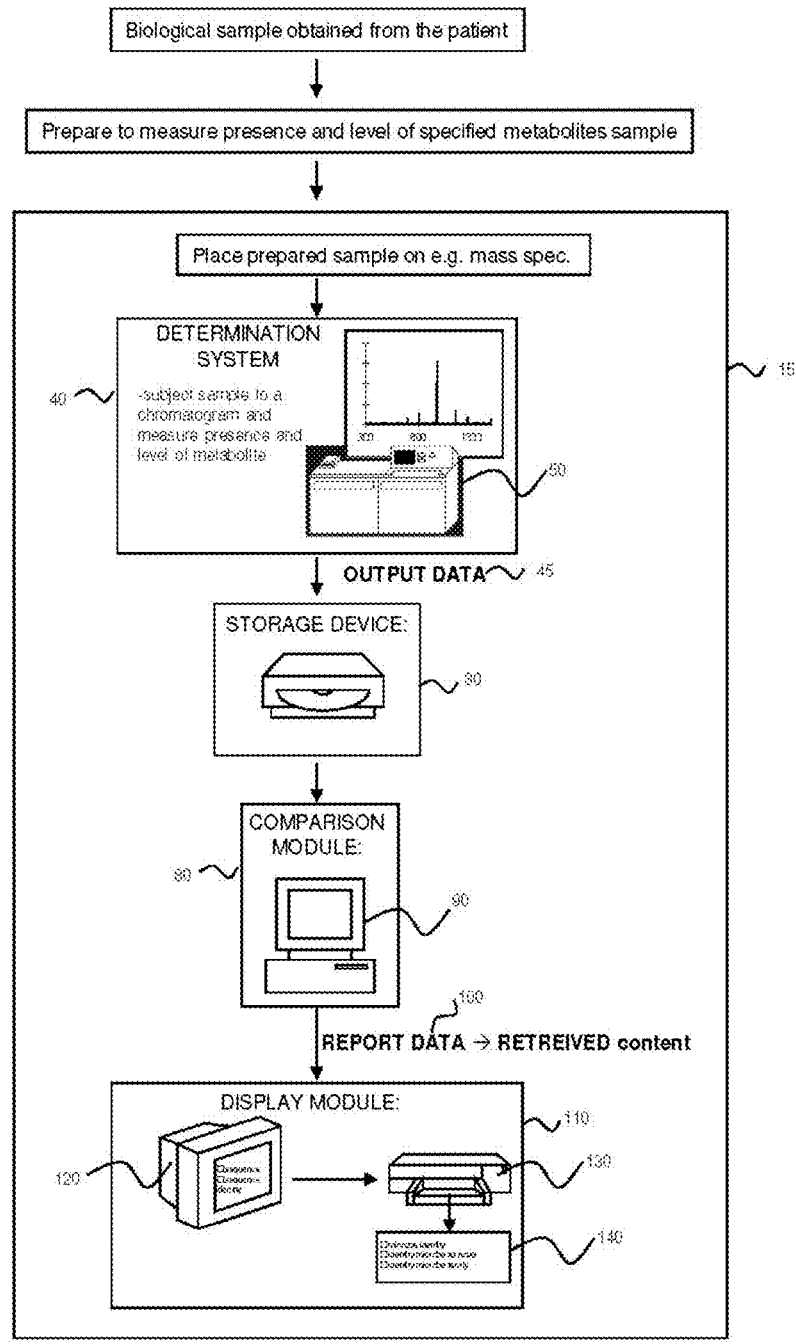
FIG. 8: An illustration of a system according to the invention for performing a method of detecting or identifying that a pregnant woman is at risk of developing pre-eclampsia.

Referring generally to FIG. 8, the computer readable storage media #30 can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable storage media may define instructions, for example, as part of one or more programs, that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable storage media on which such instructions are embodied may reside on one or more of the components of either of a system, or a computer readable storage medium described herein, may be distributed across one or more of such components.

The computer-readable storage media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a determination system #40, optionally, a storage device #30, a comparison module #80, and a display module #110. The functional modules can be executed on one, or multiple, computers, or by using one, or multiple, computer networks. The determination system has computer executable instructions to provide e.g., sequence information in computer readable form.

The determination system #40, can comprise any system for detecting at least one of the biomarkers from Table 1. Such systems will typically determine the relative abundance of the metabolite in the biological sample. Standard procedures such as UPLC-MS can be used.

Additionally one can determine other factors such as blood pressure, BMI, age, height, weight, circumference of waist, arms, legs. These factors can be used in conjunction with the biomarkers in assessing risk of pre-eclampsia.

The information determined in the determination system can be read by the storage device #30. As used herein the "storage device" is intended to include any suitable computing or processing apparatus or other device configured or adapted for storing data or information. Examples of an electronic apparatus suitable for use with the present invention include a stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon metabolite abundance information. Such information may be provided in digital form that can be transmitted and read electronically, e.g., via the Internet, on diskette, via USB (universal serial bus) or via any other suitable mode of communication.

As used herein, "stored" refers to a process for encoding information on the storage device. Those skilled in the art can readily adopt any of the presently known methods for recording information on known media to generate manufactures comprising information relating to these metabolites and other pregnancy factors.

In one embodiment the reference data stored in the storage device to be read by the comparison module is compared, e.g., level of metabolite in sample with a normal or pre-eclampsia control.

The "comparison module" #80 can use a variety of available software programs and formats for the comparison operative to compare sequence information data determined in the determination system to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to the pre-eclampsia related metabolites.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content based in part on the comparison result that may be stored and output as requested by a user using a display module #110.

The content based on the comparison result, may be from normal pregnant women. Alternatively, the content based on the comparison result may be women with pre-eclampsia.

In one embodiment of the invention, the content based on the comparison result is displayed on a computer monitor #120. In one embodiment of the invention, the content based on the comparison result is displayed through printable media #130, #140. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The methods described herein therefore provide for systems (and computer readable media for causing computer systems) to perform methods for detecting and/or identifying risk of a pregnant woman developing pre-eclampsia.

Systems and computer readable media described herein are merely illustrative embodiments of the invention for performing methods of diagnosis in an individual, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

The invention also provides a computer program which when executed on a computer causes the computer to perform a process for early detection of risk of a pregnant woman developing pre-eclampsia, the process comprising: inputting an abundance of at least one metabolite biomarker of Table 1 obtained by assaying a test biological sample obtained from the woman at 11 to 17 weeks gestation; comparing the abundance of the at least one metabolite biomarker with a reference abundance for the at least one metabolite biomarker; and determining a quantitative estimate of pre-eclampsia risk based on the comparison step.

Typically, the abundance of at least one metabolite biomarker selected from the group of 5-hydroxytryptophan, monosaccharide, decanoylcarnitine, methylglutaric acid and/or adipic acid, oleic acid, docosahexaenoic acid and/or docosatriynoic acid, γ-butyrolactone and/or oxolan-3-one, 2-oxovaleric acid and/or oxo-methylbutanoic acid, acetoacetic acid, hexadecenoyl-eicosatetraenoyl-sn-glycerol, sphingosine-1-phosphate, sphinganine-1-phosphate, and vitamin D3 derivatives, is inputted.

Ideally, the abundance of a plurality of metabolite biomarkers including 5-hydroxytryptophan, monosaccharide, decanoylcarnitine, methylglutaric acid and/or adipic acid, oleic acid, docosahexaenoic acid and/or docosatriynoic acid, γ-butyrolactone and/or oxolan-3-one, 2-oxovaleric acid and/or oxo-methylbutanoic acid, acetoacetic acid, hexadecenoyl-eicosatetraenoyl-sn-glycerol, sphingosine-1-phosphate, sphinganine-1-phosphate, and vitamin D3 derivatives, is inputted.

Preferably, step of determining the quantitative estimate of pre-eclampsia risk comprises determining the likelihood of pre-eclampsia using a multivariate analysis which typically comprises using the abundance of the or each metabolite biomarker and distribution parameters derived from a set of reference abundance values. Ideally, the multivariate analysis employs a multivariate discriminant PLS-DA model or a multivariate discriminant PC-CVA model.

The invention also provides a computer program recording medium storing a computer program according to the invention.

Methods

Participants and Specimens

The SCOPE study is a prospective, multi-centre cohort study with the main aim of developing accurate screening methods for later pregnancy complications, including preeclampsia (ACTRN12607000551493), small for gestational age (SGA) infants and spontaneous preterm birth. Full ethical approval has been obtained from local ethics committees (New Zealand AKX/02/00/364 and Australia REC 1712/5/2008) and all patients gave written informed consent. Healthy nulliparous women with a singleton pregnancy were recruited between 14 and 16 weeks and tracked throughout pregnancy.

Women attending hospital antenatal clinics, obstetricians, general practitioners or community midwives prior to 15 weeks' gestation were invited to participate in the SCOPE study. Exclusion criteria included 1) considered at high risk of preeclampsia, SGA or spontaneous preterm birth due to underlying medical conditions (chronic hypertension, diabetes, renal disease, systemic lupus erythematosus, anti-phospholipid syndrome, sickle cell disease, human immunodeficiency virus), gynaecological history, ≥3 previous terminations or ≥3 miscarriages; 2) had a known major fetal anomaly or abnormal karyotype or 3) received intervention that may modify pregnancy outcome (e.g. aspirin therapy). Participants were interviewed and examined by a research midwife at 15+1 and 20+1 weeks of gestation and underwent an ultrasound scan at 20+1 weeks. At the time of interview, data were entered into an internet accessed, central database with a complete audit trail.

Data collected at 15 weeks included detailed demographic, obstetric and medical and family information. Current pregnancy data included an early pregnancy scan to accurately calculate the estimated date of delivery. If the woman had a certain last menstrual period (LMP) date, the estimated date of delivery was only adjusted if either 1) a scan performed at <16 weeks' gestation found a difference of ≥7 days between the scan gestation and that calculated by the LMP or 2) on 20-week scan a difference of ≥10 days was found between the scan gestation and that calculated from the LMP. If her LMP date was uncertain, then scan dates were used to calculate the estimated date of delivery. Information was collected on current pregnancy complications such as vaginal bleeding and dietary information pre-conception and during pregnancy was obtained using food frequency questions. Use of folate and multivitamin, cigarettes, alcohol and recreational drugs was recorded for preconception, 1st trimester and at 15 weeks. A lifestyle questionnaire was completed by participants asking about work, exercise and sedentary activities, snoring, domestic violence and social supports. Validated psychological scales measuring perceived stress (Perceived Stress Scale), depression (Edinburgh Postnatal Depression Scale), anxiety (Short Form of the State Trait Anxiety Index measuring anxiety) and behavioural responses to pregnancy (adapted from the Behavioural Responses to Illness Questionnaire) were completed. Maternal physical measurements included two blood pressure recordings with mercury or aneroid sphygmomanometers, height, weight and the circumference of her waist, hip, arm and head. Proteinuria in a midstream urine specimen was measured by dipstick or a protein creatinine ratio. At 20±1 weeks' gestation, the information collected included any pregnancy complications since the 15 week interview, maternal physical measurements and the participant completed the lifestyle questionnaire. Ultrasound examination at 20±1 weeks included measurements of the fetus (biparietal diameter, head circumference, abdominal circumference and femur length) and Doppler studies of the umbilical and uterine arteries.

Participants were followed prospectively, with pregnancy outcome data and baby measurements collected by research midwives. Data monitoring included 1) individually checking all data for each participant, including for any data entry errors of the lifestyle questionnaire, and 2) using customised software to detect any systematic data entry errors.

Primary Outcome Measure

The primary outcome was preeclampsia, defined as gestational hypertension (systolic blood pressure ≥140 mmHg and/or diastolic blood pressure ≥90 mmHg on at least two occasions four hours apart after 20 weeks of gestation, but before the onset of labour, or postpartum systolic blood pressure ≥140 mmHg and/or diastolic blood pressure ≥90 mmHg on at least two occasions four hours apart) with proteinuria (24 hour urinary protein ≥300 mg or spot urine protein:creatinine ratio ≥30 mg/mmol creatinine or urine dipstick protein ≥2+) or any multi-system complication of preeclampsia. Multi-system complications included any of the following 1) acute renal insufficiency defined as a new increase in serum creatinine ≥100 umol/L antepartum or >130 umol/L postpartum; 2) liver involvement defined as raised aspartate transaminase and/or alanine transaminase >45 IU/L and/or severe right upper quadrant or epigastric pain or liver rupture; 3) neurological included eclampsia, imminent eclampsia (severe headache with hyper-reflexia and persistent visual disturbance) or cerebral haemorrhage and 4) haematological included thrombocytopenia (platelets <100×109/L), disseminated intravascular coagulation or haemolysis.

An uncomplicated pregnancy was defined as a pregnancy not complicated by preeclampsia, SGA, spontaneous preterm birth or any other pregnancy complication such as gestational hypertension.

Discovery Phase

In the discovery phase of the investigation, a nested case control study was performed within the initial 1628 recruits in Auckland, New Zealand, of whom pregnancy outcome was known in 1608 (98.8%). Sixty seven (4.2%) women developed preeclampsia and 1021 (63.5%) had uncomplicated pregnancies. The remainder had other pregnancy complications. Sixty women who developed preeclampsia were matched for age, ethnicity and BMI to 60 controls who had uncomplicated pregnancies. The study was limited to 120 samples to guarantee optimal signal stability from the UPLC-MS systems.[1]

Validation Phase

In the validation-phase of the investigation, a nested case control study was performed within the initial 596 recruits in Adelaide, Australia, of whom pregnancy outcome was known in 595 (99.8%). Forty six (7.7%) women developed preeclampsia and 267 (44.9%) had uncomplicated pregnancies. The remainder had other pregnancy complications. Thirty-nine women who developed preeclampsia were matched for age, ethnicity and BMI to 40 controls who had uncomplicated pregnancies.

Preeclampsia was defined as a blood pressure ≥140/90 mmHg after 20 weeks gestation (but before the onset of labor) or in the postnatal period, with either proteinuria (24 h urinary protein ≥300 mg, spot urine protein:creatinine ratio ≥30 mg/mmol or urine dipstick ≥++) and/or evidence of multi-organ complications[2].

Venipuncture was performed at 15±1 weeks' gestation, and plasma samples were collected into BD EDTA-Vacutainer® tubes, placed on ice and centrifuged at 2400×g at 4° C. according to a standardized protocol. Plasma was stored in aliquots at −80° C. The collection and storage conditions were identical for cases and controls, with the time between collection and storage being 2.07 (SD 0.90) and 2.02 (SD 0.96) hours, respectively P=0.78.

Reagents, Sample Preparation and Mass Spectral Analysis

All chemicals and reagents used were of Analytical Reagent or HPLC grade and purchased from Sigma-Aldrich (Poole, UK) or ThermoFisher Scientific (Loughborough, UK). All samples were prepared using a protein removal procedure followed by analysis using an Ultra Performance Liquid Chromatography-Mass Spectrometer (Waters ACQUITY UPLC system coupled to a ThermoFisher Scientific LTQ-Orbitrap mass spectrometer). Raw profile data was deconvolved into a peak table using XCMS software.[3] Data was then subjected to strict Quality Assurance procedures so that statistical analysis was only performed on reproducible data. Full details of all methods pertaining to sample preparation and UPLC-MS analysis are described in the attached supplementary methodology file.

Samples were prepared by reconstitution in 70 µl HPLC grade water followed by vortex mixing (15 seconds), centrifugation (11 337 g, 15 minutes) and transfer to vials. Samples were analysed by an Acquity UPLC (Waters Corp. Milford, USA) coupled to a LTQ-Orbitrap mass spectrometry system (Thermo Fisher Scientific, Bremen, Germany) operating in electrospray ionisation mode. Samples were analysed consecutively in positive ion mode followed and then consecutively in negative ion mode. Chromatographic separations were performed employing an ACQUITY UPLC BEH 1.7 µm-$C_{18}$ column (2.1×100 mm, Waters Corp. Milford, USA). Solvent A and solvent B were 0.1% formic acid in water and 0.1% formic acid in methanol, respectively. In positive ion mode a flow rate of 0.40 ml $min^{-1}$ was applied with a gradient elution profile (100% A for 1 minute and subsequently ramped to 100% B (curve 5) over 15 minutes, followed by a 4 minute hold at 100% B before a rapid return to 100% A and a hold for 2 minutes). In negative ion mode a flow rate of 0.36 ml $min^{-1}$ was applied with a gradient elution program (100% A for 2 minutes and subsequently ramped to 100% B (curve 4) over 15 minutes, followed by a 5 minute hold at 100% B before a rapid return to 100% A and a hold for 2 minutes). The column and samples were maintained at temperatures of 50° C. and 4° C., respectively. A 10 µl sample volume was introduced onto the column and 50% of the column effluent was transferred to the mass spectrometer. Centroid MS scans were acquired in the mass range of 50-1000Th using the Orbitrap mass analyser operating with a target mass resolution of 30 000 (FWHM as defined at m/z 400) and a scan time of 0.4 s. Mass calibration was performed before each analytical batch using an instrument manufacturer defined calibration mixture (ThermoFisher Scientific, Bremen, Germany).

Statistical Analysis

Comparisons of clinical data between cases and controls were performed using the Student's t-test, Mann-Whitney test, Chi square test or Fisher's Exact test, as appropriate (SAS® system 9.1).

Discovery Phase

For each metabolite peak reproducibly detected in the discovery phase study, the null hypothesis that the means of the case and control sample populations were equal was tested using either the Mann-Whitney test or Student's t-test, depending on data normality. The critical p-value for significance was set to 0.05. No correction for multiple comparisons was performed at this point as the aim was to reduce the many thousands of detected features down to a subset of potentially 'information rich' peaks while keeping the number of probable false negatives (type II error) to a minimum. False positive candidate biomarkers are identified in the validation phase of this investigation.

In order to uncover multivariate latent structure in the data, which in turn helps assess the combinatorial predictive ability of the candidate biomarkers, the significant peaks were combined into a single multivariate discriminant model using Principal Components (PC) Analysis followed by Canonical Variate Analysis (CVA) known as PC-CVA.[4] The PC stage is necessary to orthogonalize the data and reduce it down to a set of lower-dimensional latent variables. These variables (Principal Components—PCs) contain the fundamental variance structures within the data. The optimal number of PCs (and hence the most robust multivariate model) was found by employing 0.632+Bootstrap substitution[5], using 100 bootstrap samples to produce an unbiased estimate of prediction error All peak data were Pareto scaled before analysis.[6,7]

Further analysis to assess the combinatorial predictive ability of the candidate biomarkers was done by combining the significant peaks into a single multivariate discriminate model using partial leas-squares discriminant analysis (PLS-DA). The optimal number of latent factors used in the PLS-DA model was selected using stratified 5-fold cross-validation and model quality assessed during the standard $R^2$ and $Q^2$ measures, where $R^2$, the squared correlation coefficient between the dependant variable and the PLS-DA prediction, measures "goodness of fit" (a value between 0 and 1, where 1 is a perfect correlation) using all of the available data to build a given PLS-DA model. $Q^2$ provides a measure of "goodness of prediction" and is the averaged correlation coefficient between the dependent variable and the PLS-DA predictions for the 5 houdout data sets generated during cross-validation process.

Further validation was performed to check the robustness of the final PLS-DA model by comparing the $R^2$ value to a reference distribution of all of the possible modles uwing permutation testing (N=1000) following the standard protocol for metabolomic studies. Here a reference $R^2$ distribution is obtained by calculating all of the possible PLS-DA models under random reassignment of the case/control labels for each measured metabolic profile. If the correctly labeled model's $R^2$ value is close to the centre of the reference distribution, then the model performs no better than a randomly assigned model and is, therefore, invalid. For all of the PLS-DA models described here, the associated reference distribution plots are provided, from which an estimate of the probability of the candidate modle randomly occurring can be estimated. In addition, for each PLS-DA model, a receiver operator characteristic (ROC) curve was determined so that an accurate assessment of discriminatory ability could be made.

As a preprocessing step to remove any structured nose in the data set, direct orthogonal signal correction was performed using a single correction factor and a tolerance setting of $1\times10^{-3}$. All of the peak data were scaled to unit variance before multivariate analysis.

For identification of UPLC-MS related peaks, the accurate mass for each peak were searched against The Manchester Metabolomics Database[8] constructed with information from both the Human Metabolome DataBase (HMDB) (http://www.hmdb.ca/) and Lipidmaps http://www.lipidmaps.org/). A metabolite name(s) was reported when a match with a mass difference between observed and theoretical mass was less than 5 ppm. Using UPLC-MS, metabolites are often detected multiple times due to chemical adduction, dimerization, multiple-charging, isotope peaks and fragmentation. After removal of duplicate identifications, a list of unique metabolites was compiled. Definitive identifications were reported only for metabolites with retention time errors <10 seconds and an accurate mass match <5 ppm. Once identified, the metabolites were grouped into metabolite classes using the HMDB 'Class' hierarchy (http://www.hmdb.ca/).

For each named metabolite, a Receiver-Operator Characteristic (ROC) curve was determined to assess each metabolite's effectiveness as a univariate discriminatory biomarker. In addition, for each metabolite, the optimal unbiased discriminatory decision boundary was estimated using the optimal Youden's index method and then the associated discriminatory odds ratios with 95% confidence intervals (OR 95% CI) calculated.[9-10]

Validation Phase

The identified metabolites found to be significant in the discovery phase study were matched to the metabolite peaks detected in the validation study. If a match was found, then the metabolite was univariately assessed as a potential biomarker using the same protocol as for the discovery stage. In addition, a PC-CVA and/or PLS-DA model was constructed to assess the multivariate discriminatory ability of the validation peaks.

Finally, an 'optimal' multivariate discriminatory model drawn from the named metabolites observed in both the discovery and validation studies was searched for. A Genetic Algorithm-based search program was used to obtain the subset of metabolites which produced an effective predictive rule for the onset of PE. This search method has been shown to be very successful in previous studies.[11,12,13,14,15,16] In this algorithm a set of candidate solutions evolve over time toward an optimal state. The evolution is pushed by computational techniques inspired by evolutionary biology. In the algorithm devised by the inventors, each candidate solution (subset of metabolites) is assessed by building two independent Linear Discriminant Analysis models, one modeling the discovery data, and the other modeling the validation data. A candidate's fitness is proportional to the sum of the Root Mean Square Error of Prediction (RMSEP) of these two models. Once the optimal subset of metabolites was found, its predictive ability was assessed using Canonical Variate Analysis/ Partial Least-Squares Discriminant Analysis and Hotelling's T-square test.[4] Assessment was performed independently for the discovery and validation data.

All statistical analyses were carried out using the Matlab® scripting language (http://www.mathworks.com/). All univariate algorithms were implemented such that any missing values are ignored. All multivariate algorithms were implemented such that missing values were imputed using the nearest-neighbor method.[17] The Genetic Algorithm search program was written in-house.[11] Scripts are available upon request.

Results

Discovery Phase

Figure 1:
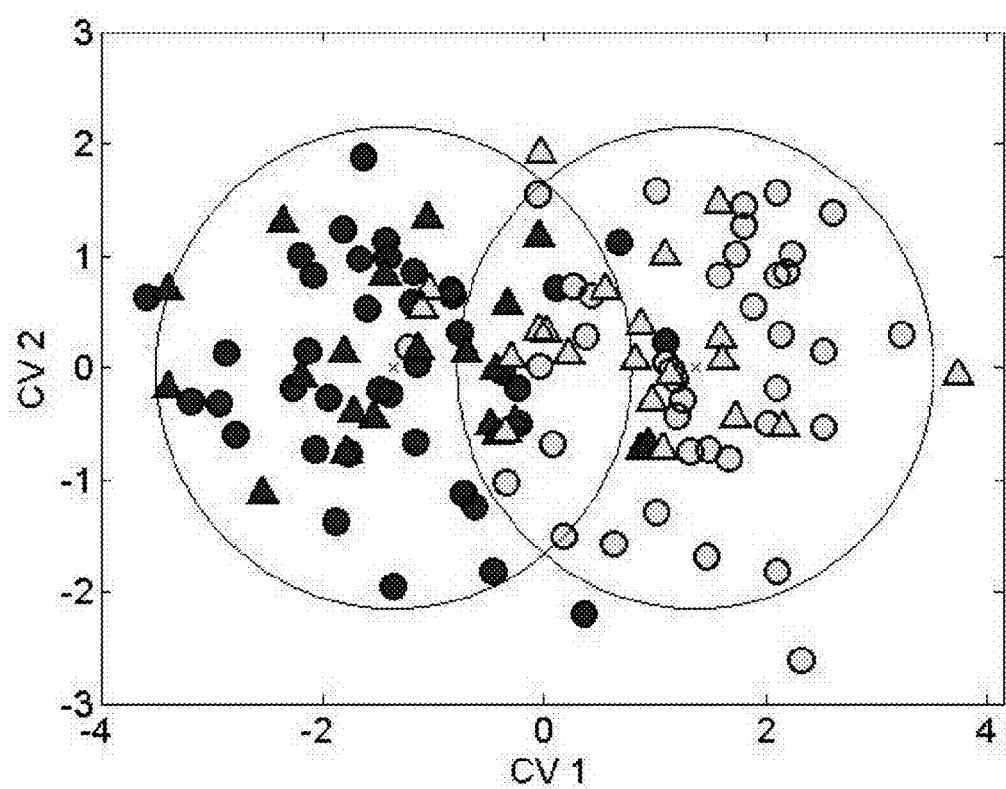
FIG. 1: The scores plot for a PC-CVA model using the optimal number of Principal Components (n=35). Model construction was performed in a training dataset (67% of samples, circles) and tested on a hold out dataset (33% of samples, triangles) taken from the 'discovery' set of samples. Black=preeclampsia; Grey=controls. CV1 can be considered as the weighted linear combination of the 'information rich' peaks which best discriminate between the preeclampsia and control samples. Circled area is 95% $\chi^2$ confidence regions calculated from the training data scores.

Maternal characteristics and pregnancy outcome in the women with preeclampsia and controls are shown in Table 2. After quality assurance, and univariate screening, the UPLC-MS analysis revealed 457 information-rich metabolite peaks. A multivariate discriminant model (PC-CVA) using these 457 peaks proved to discriminate well, producing an area under the ROC curve of 0.96 with an odds ratio 68 (95% CI 21-216). This was far better than any individual metabolite peak. Model selection was performed using the 0.632+ bootstrap resampling method. FIG. 1 shows the PC-CVA scores plot, where a third of the samples were randomly removed from the modeling process and used as a test set. The distribution of the test set model predications was similar to the training set, and only 10% of the test set data was outside the respective 95% confidence region; this suggests there was robust multivariate discriminatory information within these data.

Figure 3:
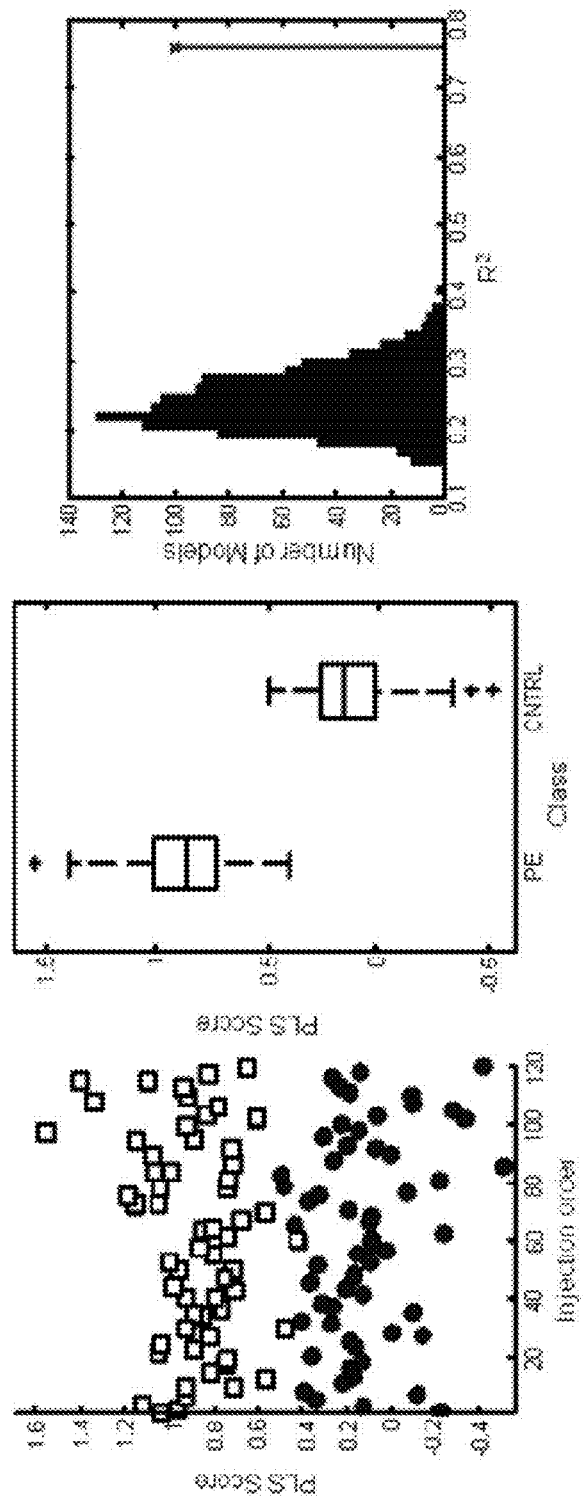
FIG. 3: The scores plot for a PLS-DA model using the optimal number of latent vectors (n=1) for data taken from the "discovery" nested case-control study (light grey indicates pre-eclampsia; dark grey indicates controls). Model construction was performed using 5-fold cross-validation resulting in an $R^2$ of 0.76 and a $Q^2$ of 0.68. The $R^2$ distribution plot shows that the chosen model's $R^2$ value is significantly distant from the $H_0$ randomly classified permutation distribution (n=1000); thus the probability of the presented model randomly occurring is <0.001. Partial least-squares (PLS) score can be considered sas the weighted linear combination of the "information-rich" peaks, which best discriminate between the preeclampsia and control samples. AUC curve was 0.99.

Further analysis using the multivariate discriminant model PLS-DA resulted in a model having an $R^2$ of 0.76, $Q^2$ of 0.68, and area under the ROC curve (AUC) of 0.99. Model selection was performed using 5-fold cross-validation, and the final model was further validated using permutation testing. The final model used a single latent factor and the probability of this model randomly occurring was <0.001. FIG. 3 shows the PLS-DA scores plot and the permutation testing.

Of the 457 metabolite peaks detected by the UPLC-MS, 70 were successfully identified chemically as known metabolites, of which 45 were 'unique' in the sense of being defined molecular entities (Table 1). When grouped into metabolite classes (based on the Human Metabolome Database (HMDB)) eleven clear classes emerged. These were: amino acids (AA), carbohydrates (Cb), carnitines (Cam), Eicosanoids (Eic), fatty acids (FA), keto or hydroxy acids (KHA), lipids (Lip), phospholipids (PL), porphyrins (Por), phosphatidylserine (PS) and steroids (St).

Figure 4:
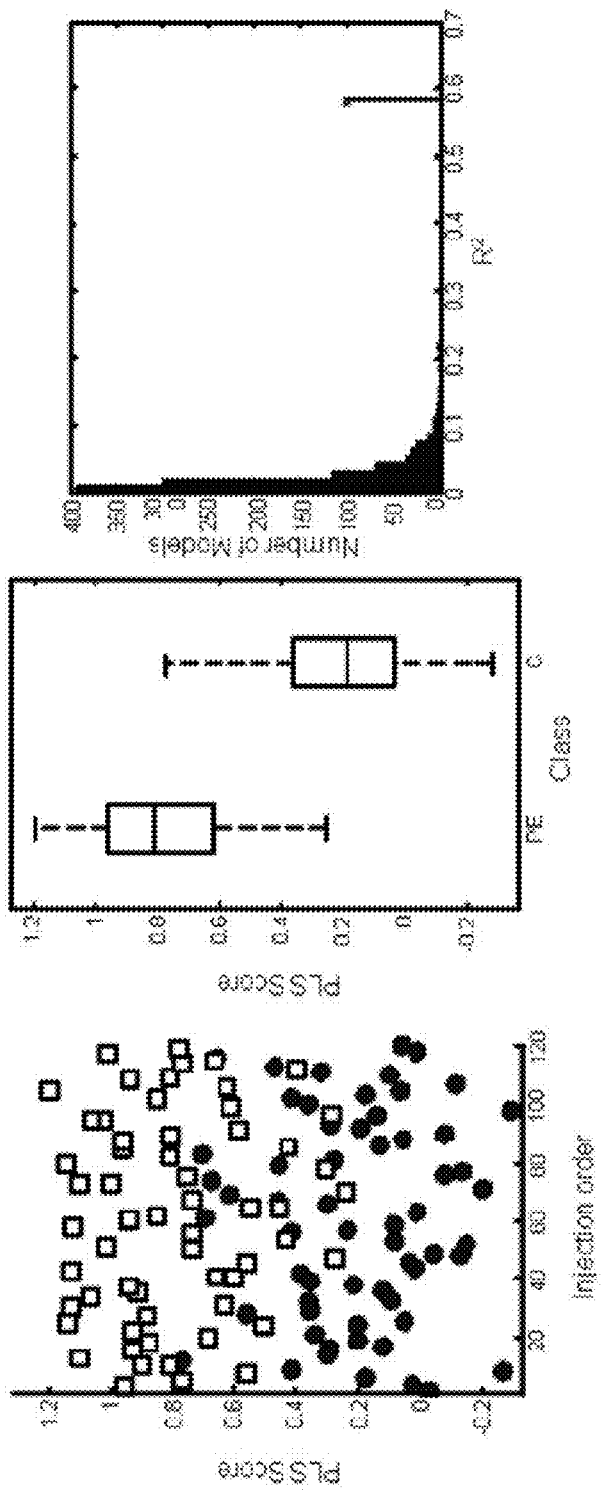
FIG. 4: The scores plot for a PLD-DA model using the optimal number of Latent Vectors (n=1) for the 45 named metabolites taken from the 'discovery' nested case-control study. Grey=preeclampsia; Black=controls. Model construction was performed using 5-fold cross validation resulting in an $R^2$=0.58 and $Q^2$=0.57. The $R^2$ distribution plot shows that the chosen model's $R^2$ value is significantly distant from the $H_o$ randomly classified permutation distribution (n=1000); thus the probability of the presented model randomly occurring is <0.001. Area under ROC curve was 0.96.

A PC-CVA model was built using only the 45 named metabolites. This produced an area under the ROC curve of 0.90 and the odds ratio 23.5 (95% CI 21-216). Similarly for a PLS-DA model built using the 45 named metabolites (1 latent factor), a predictive model with $R^2$ of 0.58, $Q^2$ of 0.57 and AUC of 0.96 (FIG. 4). These results proved to be only a slight reduction of diagnostic performance when compared to the full 457-peak model.

Validation Phase

The maternal characteristics and pregnancy outcome in the women with preeclampsia and controls are shown in Table 2—Characteristics and pregnancy outcome of women who later developed preeclampsia and controls.

TABLE 2

| | AUCKLAND | | | ADELAIDE | | |
|---|---|---|---|---|---|---|
| | Preeclampsia n = 60 | Controls n = 60 | P Value | Preeclampsia n = 39 | Controls n = 40 | P Value |
| Maternal Characteristics | | | | | | |
| Age (years) | 30.2 (4.9) | 30.4 (4.7) | 0.79 | 22.0 (4.8) | 23.2 (5.3) | 0.30 |
| Ethnicity | | | | | | |
| Caucasian | 46 (77%) | 52 (87%) | 0.16 | 39 (100%) | 39 (97.5%) | 1.0 |
| Other | 14 (23%) | 8 (13%) | | 0 (0%) | 1 (2.5%) | |
| At 15 weeks gestation | | | | | | |
| Body mass index (kg/m$^2$) | 27.3 (4.9) | 26.0 (3.9) | 0.12 | 27.5 (6.2) | 26.7 (4.6) | 0.48 |
| Systolic blood pressure (mmHg) | 115 (11) | 107 (12) | 0.0003 | 113 (11) | 108 (10) | 0.05 |
| Diastolic blood pressure (mmHg) | 72 (9) | 63 (9) | <0.0001 | 67 (7) | 65 (7) | 0.17 |
| Current smoker | 1 (1.7%) | 4 (6.7%) | 0.36 | 11 (28.2%) | 12 (30%) | 0.86 |
| Gestation at blood sampling (wks) | 15.0 (0.9) | 15.0 (0.8) | 0.59 | 15.2 (0.7) | 15.0 (0.7) | 0.19 |
| Pregnancy Outcome | | | | | | |
| Systolic blood pressure (mmHg) | 156 (15) | 119 (9) | <0.0001 | 158 (10) | 124 (8) | <0.0001 |
| Diastolic blood pressure (mmHg) | 103 (8) | 74 (9) | <0.0001 | 99 (10) | 74 (7) | <0.0001 |
| Proteinuria* | 54 (90%) | — | — | 32 (82%) | — | — |
| Protein Creatinine Ratio (mg/mmol) | 70 (42, 117) n = 53 | — | — | 52 (26, 172) n = 38 | — | — |
| 24 h Proteinuria (g) | 0.6 (0.4, 1.2) n = 42 | — | — | 0.7 (0.2, 2.2) n = 14 | — | — |
| Severe preeclampsia | | | | | | |
| Severe hypertension | 20 (33.3%) | — | — | 6 (15.4%) | — | — |
| Thrombocytopenia | 7 (11.7%) | — | — | 2 (5%) | — | — |
| Liver Involvement | 12 (20.0%) | — | — | 11 (28%) | — | — |
| Renal Involvement | 7 (11.7%) | — | — | 2 (5%) | — | — |
| Imminent eclampsia | 4 (6.7%) | — | — | 2 (5%) | — | — |
| Gestation at delivery (wks) | 37.5 (2.8) | 40.1 (1.1) | <0.0001 | 38.1 (2.3) | 40.0 (1.3) | <0.0001 |
| Preterm Delivery (<37 wks) | 21 (35%) | — | — | 8 (21%) | — | — |
| Birthweight (g) | 2925 (753) | 3628 (415) | <0.0001 | 3057 (784) | 3583 (391) | 0.0004 |

TABLE 2-continued

| | AUCKLAND | | | ADELAIDE | | |
|---|---|---|---|---|---|---|
| | Preeclampsia n = 60 | Controls n = 60 | P Value | Preeclampsia n = 39 | Controls n = 40 | P Value |
| Customized birthweight centile | 40 (11, 70) | 50 (35, 75) | 0.02 | 40 (9, 76) | 47 (36, 67) | 0.24 |
| Small for gestational age | 15 (25%) | — | — | 10 (25.6%) | — | — |

(Values are mean (SD), median (interquartile range) or number (%).
*Defined as dipstick >=2+ or PCR >=30 mg/mmol or 24 h urinary protein >=0.3 g/24 h)

Figure 5:
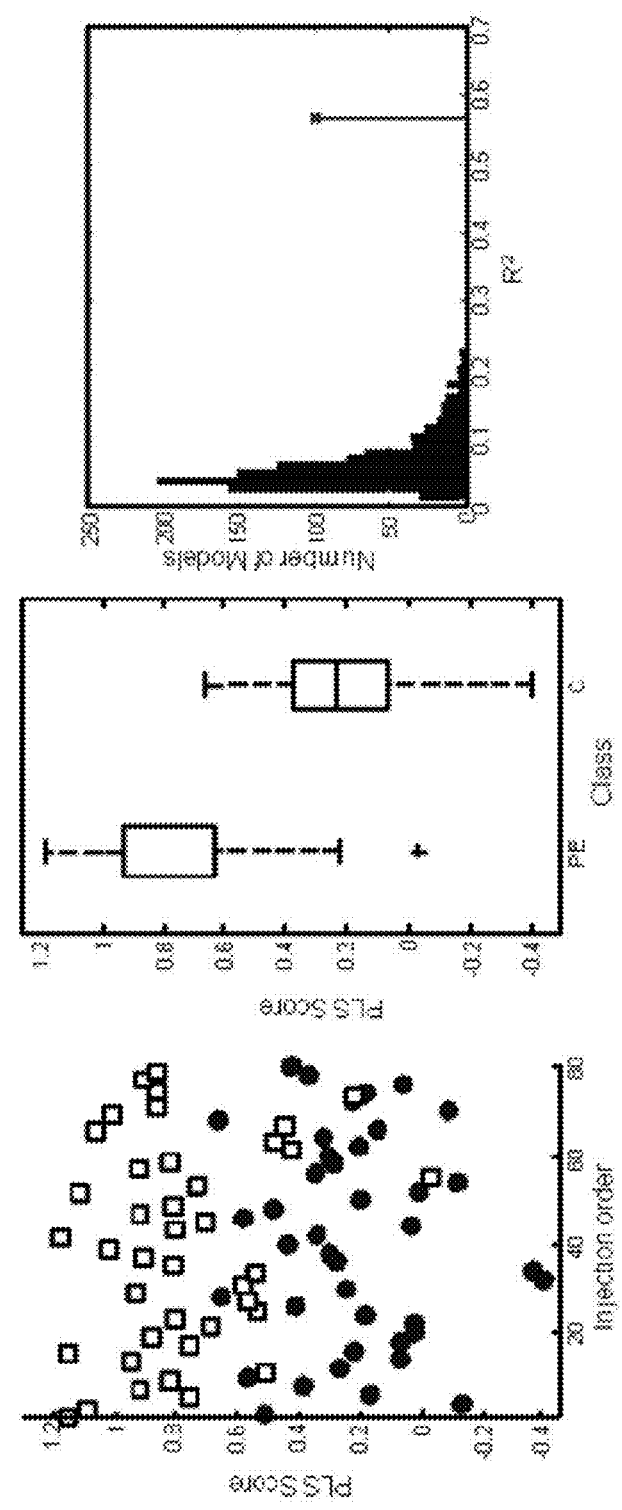
FIG. 5: The scores plot for a PLD-DA model using the optimal number of Latent Vectors (n=1) for 38 named metabolites taken from the 'validation' nested case-control study. The 38 metabolites were those of the 45 metabolites named in the discovery study that were detected in the validation study. Grey=preeclampsia; Black=controls. Model construction was performed using 5-fold cross validation resulting in an $R^2$=0.57 and $Q^2$=0.53. The $R^2$ distribution plot shows that the chosen model's $R^2$ value is significantly distant from the $H_o$ randomly classified permutation distribution (n=1000); thus the probability of the presented model randomly occurring is <0.001. Area under ROC curve was 0.95.

Of the 45 significant metabolites named in the discovery study, 34 were also detected in the validation study. All these metabolites showed similar changes in peak response (29 were raised in patients who went on to develop PE; 5 were lowered). The multivariate PC-CVA model using the 34 metabolites proved to be reasonably predictive with an AuROC of 0.86 and odds ratio of 15 (95% CI 4.4-50.6). A PLS-DA model using the 34 metabolites (1 latent factor) proved to be predictive, with $R^2$ of 0.57, $Q^2$ of 0.53 and AUC of 0.95 (FIG. 5).

Metabolite Signature of PE

Figure 2A:
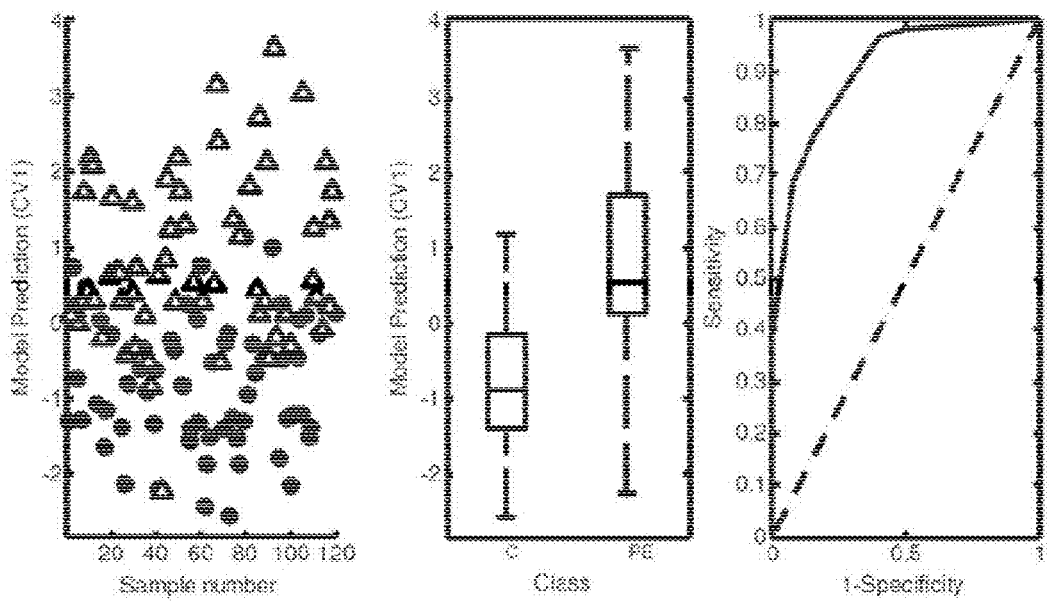
FIG. 2: The CVA model predictions for the final 14-metabolite rule found by the Genetic Algorithm Search program [C, controls, black circles; PE, preeclampsia, grey triangles] (a) Model predictions for the discovery phase data. AuROC=0.90, Odds Ratio=16.4 (95% CI 6.6–40.6), Hotelling's T-square p-value=$2\times10^{-6}$. (b) Model predictions for the validation data. AuROC=0.90, Odds Ratio=39.5 (95% CI 8.2–189.4), Hotelling's T-square p-value=$2\times10^{-3}$.
Figure 2B:
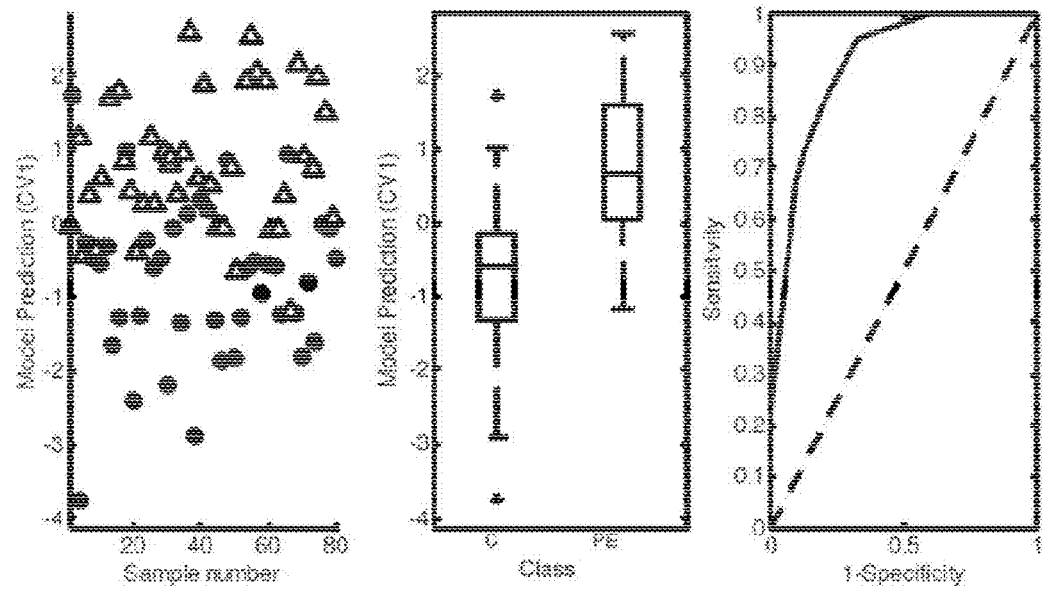
Figure 6A:
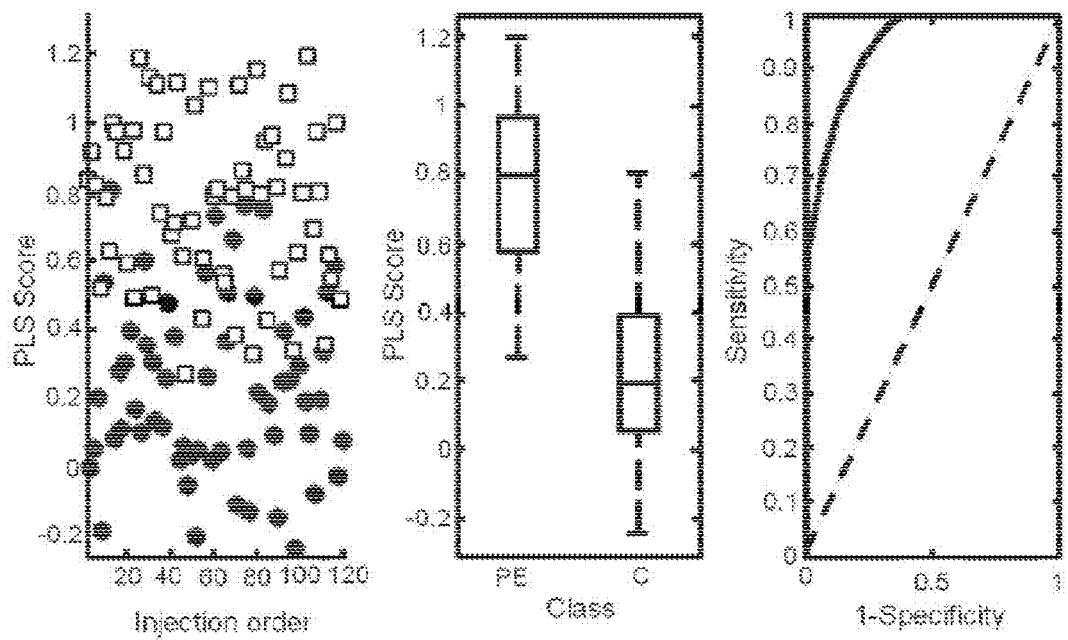
FIG. 6: The PLS-DA model predictions for the final 14-metabolite signature found by the Genetic Algorithm Search program [C, controls, black circles; PE, preeclampsia, grey squares] (a) Model predictions for the discovery phase data; $R^2$=0.54, $Q^2$=0.52, and AUC of 0.94, an Optimal Odds Ratio=36 (95% CI: 12 to 108), and Hotelling's T-square P-value=$2\times10^{-6}$. (b) Model predictions for the validation data; $R^2$=0.43, $Q^2$=0.39, and AUC of 0.92, an Optimal Odds Ratio=23 (95% CI: 7 to 73), and Hotelling's T-square P-value=$2\times10^{-3}$.
Figure 6B:
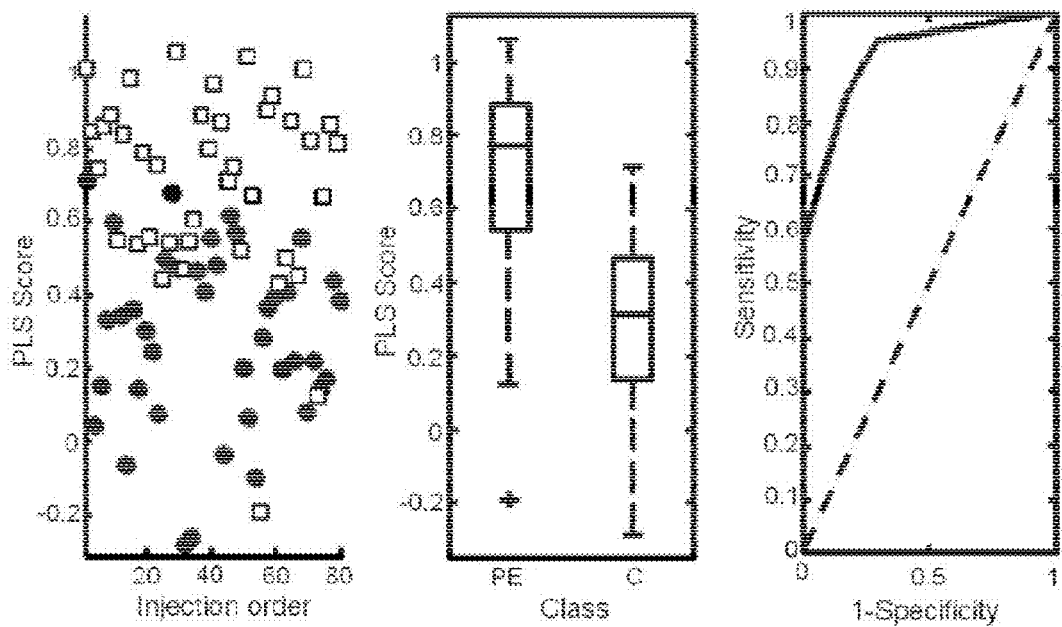
Figure 7:
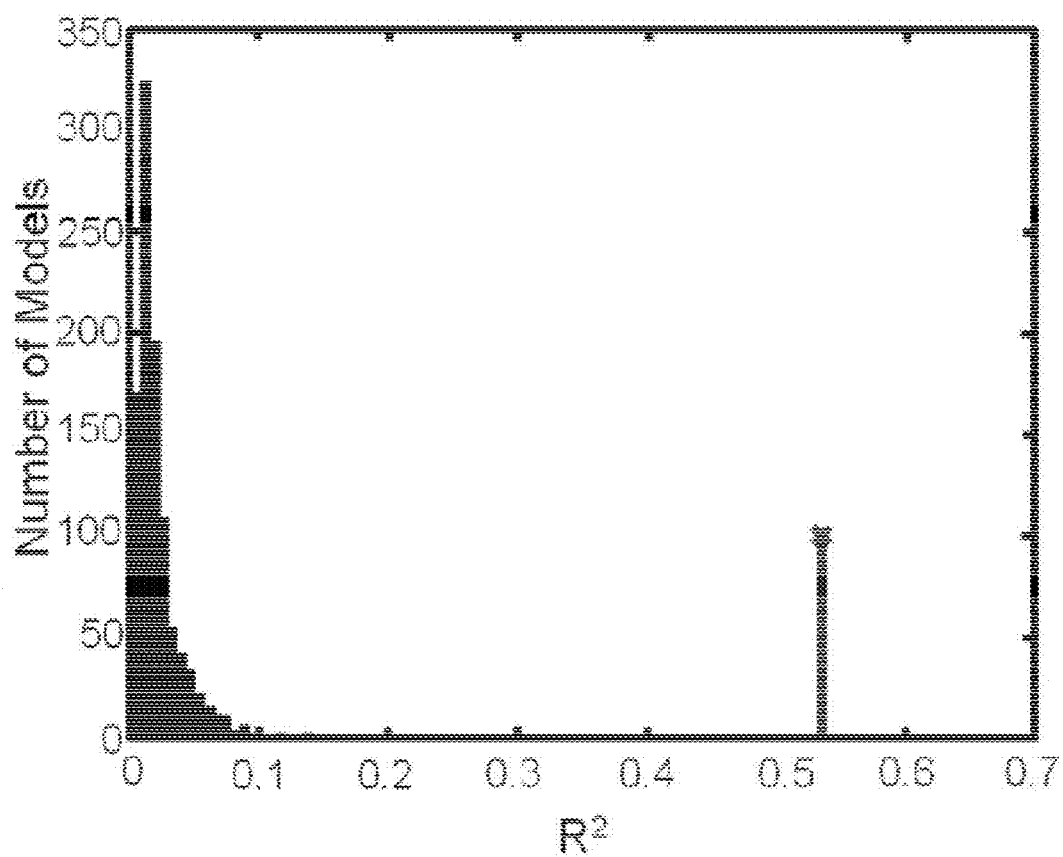
FIG. 7: The $R^2$ distribution plots for (a) the 14 metabolite discovery model and (b) the 14 metabolite validation model. Both show that the chosen models' $R^2$ values are significantly distant from the $H_o$ randomly classified permutation distribution (n=1000); thus the probability of the presented model randomly occurring is <0.001.
Figure 7:
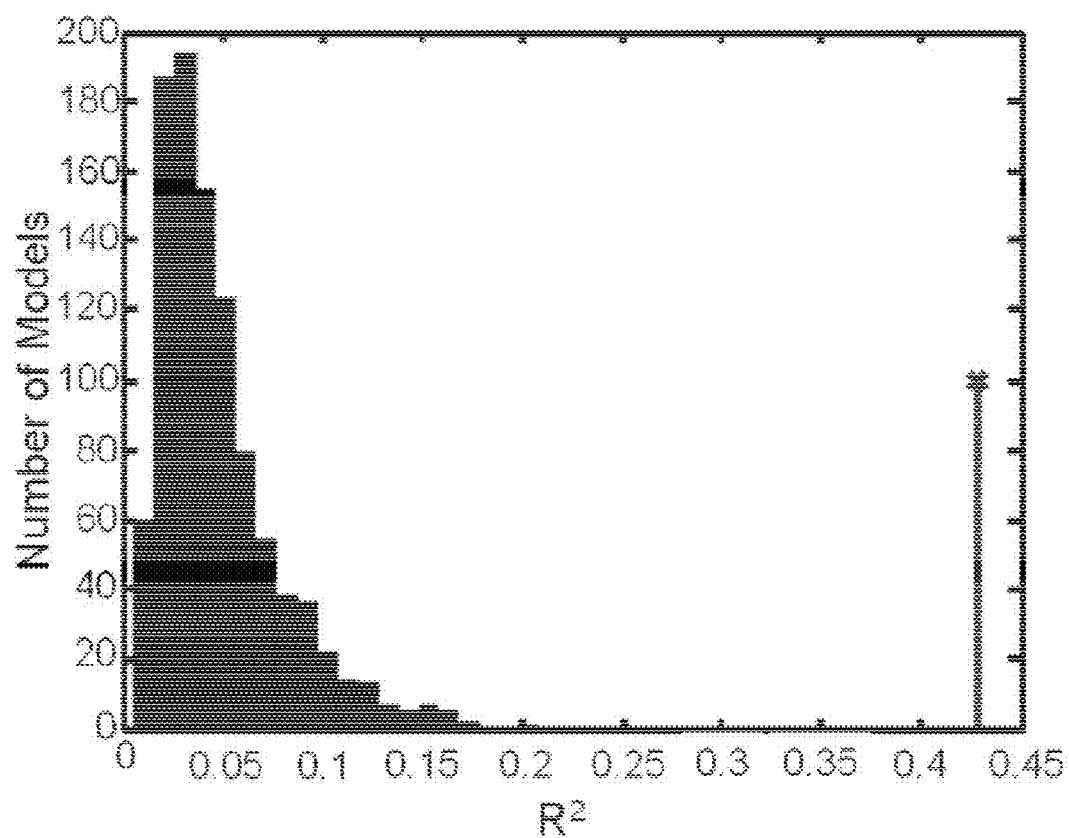

Finally, the data from both studies were mined using a Genetic Algorithm-based search program to find the subset of named metabolites which produced the most robust predictive general model. The Genetic Algorithm chose 13 metabolites (Preferred Metabolites). FIG. 2 shows the CVA model predictions using these metabolites for both the discovery study and the validation study. The AuROC for both models was 0.90 and the odds ratios were 16.4 (95% CI 6.6–40.6) and 39.5 (95% CI 8.2–189.4) for discovery and validation data respectively. In addition, FIG. 6 shows the PLS-DA model predictions had an $R^2$ of 0.54, $Q^2$ of 0.52 and AUC of 0.94, and an optimal odds ratio of 36 (95% CI: 12 to 108) for the discovery study, and an $R^2$ of 0.43, $Q^2$ of 0.39 and AUC of 0.92, and an optimal odds ratio of 23 (95% CI: 7 to 73) for the validation study. Permutation testing showed that the probability of both of the PLS-DA models randomly occurring was <0.001 (FIG. 7). The combined effect of the 13 metabolites was also tested using the Hotelling's T-square statistic. For the discovery study data, this produced a p-value of $2 \times 10^{-6}$, and for the validation study data, a P-value of 0.006. The P-values were obviously affected by the differing sample sizes (Discovery n=120; Validation N=79).

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk. The carrier may be an electrical or optical signal which may be transmitted via an electrical or an optical cable or by radio or other means.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described which may be varied in construction and detail without departing from the spirit of the invention.

REFERENCES

1 Zelena, E. et al. Development of a robust and repeatable UPLC-MS method for the long-term metabolomic study of human serum. *Anal Chem* 81, 1357-1364 (2009).
2 Brown, M. A. et al. The detection, investigation and management of hypertension in pregnancy: full consensus statement. *Aust N Z J Obstet Gynaecol* 40, 139-155 (2000).
3 Smith, C. A., Want, E. J., O'Maille, G., Abagyan, R. & Siuzdak, G. XCMS: processing mass spectrometry data for metabolite profiling using nonlinear peak alignment, matching, and identification. *Anal Chem* 78, 779-787 (2006).
4 Krzanowski, W. J. *Principles of Multivariate Analysis: A User's Perspective*. (Oxford University Press, 1988).
5 Efron, B. & Tibshirani, R. J. Improvements on cross-validation: The 0.632+ bootstrap method. *Journal of the American Statistical Association* 92, 548-560 (1997).
6 Eriksson, L., Johansson, E., Kettaneh-Wold, N. & Wold, S. *Introduction to Multi-and Megavariate Data Analysis using Projection Methods (PCA & PLS)*. (Umetrics A B, 1999).
7 van den Berg, R. A., Hoefsloot, H. C., Westerhuis, J. A., Smilde, A. K. & van der Werf, M. J. Centering, scaling, and transformations: improving the biological information content of metabolomics data. *BMC Genomics* 7, 142, doi:1471-2164-7-142 [pii] 10.1186/1471-2164-7-142 (2006).
8 Brown, M. et al. Mass spectrometry tools and metabolite-specific databases for molecular identification in metabolomics. *Analyst* 134, 1322-1332 (2009).
9 Youden, W. J. Index for rating diagnostic tests. Cancer 3, 32-35 (1950).
10 Perkins, N. J. & Schisterman, E. F. The inconsistency of "optimal" cutpoints obtained using two criteria based on the receiver operating characteristic curve. *Am J Epidemiol* 163, 670-675 (2006).
11 Broadhurst, D., Goodacre, R., Jones, A., Rowland, J. J. & Kell, D. B. Genetic algorithms as a method for variable selection in multiple linear regression and partial least squares regression, with applications to pyrolysis mass spectrometry. *Analytica Chimica Acta* 348, 71 -86 (1997).
12 Cavill, R. et al. Genetic algorithms for simultaneous variable and sample selection in metabonomics. *Bioinformatics* 25, 112-118 (2009).
13 Allen, J. et al. High-throughput classification of yeast mutants for functional genomics using metabolic footprinting. *Nat Biotechnol* 21, 692-696 (2003).
14 Jarvis, R. M. & Goodacre, R. Genetic algorithm optimization for pre-processing and variable selection of spectroscopic data. *Bioinformatics* 21, 860-868 (2005).

15 Kell, D. B. Metabolomics and machine learning: explanatory analysis of complex metabolome data using genetic programming to produce simple, robust rules. *Mol Biol Rep* 29, 237-241 (2002).

16 Goodacre, R. & Kell, D. B. in *Metabolic profiling: its role in biomarker discovery and gene function* eds G. G Harrigan & R. Goodacre) 239-256 (Kluwer Academic Publishers, 2003).

17 Speed, T. *Statistical Analysis of Gene Expression Microarray Data*. (Chapman and Hall/CRC, 2003).

The invention claimed is:

1. A method of early treatment of pre-eclampsia in a pregnant woman comprising:
    (i) obtaining a blood sample from the pregnant woman at 11-17 week gestation;
    (ii) measuring a level of Di-(octadecadienoyl)-sn-glycerol in the blood sample;
    (iii) comparing the level of Di-(octadecadienoyl)-sn-glycerol to a reference level; and
    (iv) administering an anti-hypertensive medicament to the pregnant woman if the level of Di-(octadecadienoyl)-sn-glycerol is above the reference level.

* * * * *